United States Patent
Momose et al.

(10) Patent No.: US 9,417,178 B2
(45) Date of Patent: Aug. 16, 2016

(54) MICROCHIP

(75) Inventors: Shun Momose, Kyoto (JP); Hiroki Takeuchi, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 25 days.

(21) Appl. No.: 13/993,172

(22) PCT Filed: Dec. 13, 2011

(86) PCT No.: PCT/JP2011/078814
§ 371 (c)(1),
(2), (4) Date: Jun. 11, 2013

(87) PCT Pub. No.: WO2012/081583
PCT Pub. Date: Jun. 21, 2012

(65) Prior Publication Data
US 2013/0266483 A1    Oct. 10, 2013

(30) Foreign Application Priority Data

Dec. 14, 2010    (JP) .................... 2010-277838

(51) Int. Cl.
| | | |
|---|---|---|
| G01N 21/01 | (2006.01) | |
| B01L 3/00 | (2006.01) | |
| G01N 33/487 | (2006.01) | |
| G01N 35/00 | (2006.01) | |

(52) U.S. Cl.
CPC .......... *G01N 21/01* (2013.01); *B01L 3/502753* (2013.01); *G01N 33/487* (2013.01); *B01L 2200/0605* (2013.01); *B01L 2200/0621* (2013.01); *B01L 2300/0816* (2013.01); *B01L 2400/0409* (2013.01); *B01L 2400/0457* (2013.01); *G01N 2035/00158* (2013.01)

(58) Field of Classification Search
None
See application file for complete search history.

(56) References Cited

U.S. PATENT DOCUMENTS

| | | | |
|---|---|---|---|
| 4,883,763 A * | 11/1989 | Holen et al. | ..................... 436/45 |
| 2008/0138890 A1* | 6/2008 | Horiike et al. | ............. 435/288.7 |
| 2009/0098658 A1 | 4/2009 | Momose et al. | |
| 2009/0191643 A1 | 7/2009 | Boehm et al. | |
| 2009/0291025 A1* | 11/2009 | Aoki | ........................... 422/68.1 |
| 2010/0074801 A1 | 3/2010 | Saiki | |

FOREIGN PATENT DOCUMENTS

| | | |
|---|---|---|
| JP | 2008101984 | 5/2008 |
| JP | 2009-133805 | 6/2009 |
| JP | 2010-505096 | 2/2010 |
| JP | 2010-243373 | 10/2010 |
| WO | 2008/053743 | 5/2008 |

OTHER PUBLICATIONS

Japanese Patent Office, International Search Report for International Patent Application PCT/JP2011/078814 (Jan. 24, 2012).

* cited by examiner

*Primary Examiner* — Jill Warden
*Assistant Examiner* — Julie Tavares
(74) *Attorney, Agent, or Firm* — Fish & Richardson P.C.

(57) ABSTRACT

A microchip including a fluid circuit therein and a specimen inlet for introducing a specimen containing a first component and a second component different in specific gravity from each other into the fluid circuit is provided, in which the fluid circuit includes a specimen measurement unit connected to the specimen inlet and having a prescribed volume for measuring the specimen introduced through the specimen inlet and a separation unit which is a site connected to the specimen measurement unit and having a capacity capable of storing the total amount of the measured specimen, for storing the total amount of the measured specimen and separating the first component and the second component in the stored specimen from each other.

2 Claims, 20 Drawing Sheets

(a)

(b)

(a)

(b)

(a)

600

(b)

701
700
420
600

(a)

(b)

(a)

(b)

(a)

600

(b)

441a (a)

(b)

(a)

332b (b)

(a)

(b)

811

OPTICAL MEASUREMENT (a)

(b)

MICROCHIP

TECHNICAL FIELD

The present invention relates to a microchip useful for μ-TAS (Micro Total Analysis System) and the like, suitably used in environmental analysis, chemical synthesis, and biochemical assays of DNA, protein, cells, immunity, blood, and the like.

BACKGROUND ART

In line with the recent increase in the importance of detecting or quantifying chemical substances and biological substances such as DNA (Deoxyribo Nucleic Acid), enzyme, antigen, antibody, protein, virus, cells, and the like in the field of medical care, health, food product, development of medicine, and the like, various biochips and microchemical chips (hereinafter collectively referred to as a microchip) that allow measurement thereof in a simplified manner have been proposed.

A microchip has many advantages in that a series of experiments and analytical operations carried out at laboratories can be performed within a chip that is approximately from several cm to 10 cm square and from several mm to several cm in thickness and accordingly only a small amount of specimen and reagent is required, reduction in cost is achieved, a reaction speed is fast, tests or analysis can be performed with high throughput, and test results can be obtained immediately at the site where the specimen has been collected.

A microchip has a fluid circuit therein. The fluid circuit is mainly constituted, for example, of such sites as a liquid reagent receptacle unit for holding a liquid reagent to be mixed with or caused to react to a specimen (for example, blood) to be tested or analyzed, or for treating the specimen, a measurement unit for measuring the specimen or the liquid reagent, a mixing unit for mixing the specimen and the liquid reagent, and a detection unit for testing or analyzing the liquid mixture, as well as minute channels appropriately connecting these sites.

In use, a microchip is typically mounted on an apparatus that can apply centrifugal force to the chip. By applying centrifugal force to the microchip in an appropriate direction, measurement of a specimen (or a specific component in the specimen) and/or a liquid reagent, mixing of the specimen (or the specific component in the specimen) and the liquid reagent, as well as introduction of the obtained liquid mixture to the detection unit, or the like, can be carried out. It is noted that such treatment as transfer from one site to another site, measurement, and mixing of various liquids (a specimen, a specific component in the specimen, a liquid reagent, or a mixture or a reactant of two or more types thereof, and the like) performed within a microchip may hereinafter be referred to as "fluid treatment".

For example, Japanese Patent Laying-Open No. 2009-133805 (PTD 1) discloses a microchip suitably used as a blood test chip. The microchip disclosed in this document includes a hemocyte separation unit for separating a hemocyte component from whole blood introduced within the microchip and extracting a plasma component as a part of a fluid circuit, and allows a test using only the plasma component.

CITATION LIST

Patent Document

PTD 1: Japanese Patent Laying-Open No. 2009-133805

SUMMARY OF INVENTION

Technical Problem

FIG. 28 is a top view and a bottom view each showing in an enlarged manner, a part of a second substrate forming a microchip including fluid circuits in two layers described in PTD 1 (FIGS. 3 to 4 and 6 to 12). FIG. 28 (a) is a diagram of the second substrate viewed from above, which shows a first fluid circuit (an upper fluid circuit) of the microchip and a position of a liquid (such as a specimen) present therein. FIG. 28 (b) is a diagram of the second substrate viewed from below, which shows a second fluid circuit (a lower fluid circuit) of the microchip and a position of a liquid (such as a specimen) present therein. It is noted that FIG. 28 (b) shows the second fluid circuit in a mirror-reversed manner for clear understanding of correspondence with the first fluid circuit shown in FIG. 28 (a).

An example of fluid treatment using the microchip described in PTD 1 will be described with reference to FIG. 28 by way of example of a case where whole blood is employed as a specimen. Initially, after whole blood 600' is introduced from a specimen inlet 120', centrifugal force is applied to the microchip downwardly in FIG. 28. Thus, whole blood 600' moves to the second fluid circuit through a through hole 20a' and then it is introduced in a hemocyte separation unit 420' through a flow rate restriction unit 700' [see FIG. 28 (b)]. The whole blood introduced in hemocyte separation unit 420' is centrifuged by the downward centrifugal force above and separated into a plasma component (an upper layer) and a hemocyte component (a lower layer). On the other hand, the whole blood overspilt from hemocyte separation unit 420' moves to the first fluid circuit through a through hole 20b' and is stored in a waste reservoir 430' [see FIG. 28 (a)]. FIGS. 28 (a) and (b) each show a state at the time when the above fluid treatment is performed (corresponding to FIG. 6 of PTD 1).

The microchip in PTD 1 having the fluid circuits constructed as above had a room for improvement as follows. Namely, the microchip in PTD 1 is designed such that flow rate restriction unit 700' is provided above hemocyte separation unit 420' and a channel width thereof is narrowed to restrict a flow rate and a liquid width of whole blood 600' at the time of introduction into hemocyte separation unit 420', so that whole blood 600' is reliably guided into hemocyte separation unit 420' and hemocyte separation unit 420' is filled with whole blood 600'. Owing to the narrow channel width of flow rate restriction unit 700', however, what is called "pre-separation" that whole blood 600' is centrifuged in flow rate restriction unit 700' by the time a total amount of whole blood 600' passes through flow rate restriction unit 700' and the whole blood is separated into a layer high in a ratio of the plasma component and a layer high in a ratio of the hemocyte component has occurred in some cases. When whole blood 600' which has experienced pre-separation is introduced in hemocyte separation unit 420', the whole blood having a hemocyte concentration higher than an actual hemocyte concentration (a hemocyte concentration in the taken whole blood which is to be tested) is stored in hemocyte separation unit 420', and the whole blood having a hemocyte concentration lower than an actual hemocyte concentration is overspilt from hemocyte separation unit 420' and stored in waste reservoir 430'. If such fluctuation in content of a component occurs, a plasma component in an amount necessary for fluid treatment to be performed in the microchip cannot be obtained (a hemocyte component is included in a plasma component to be sent to specimen measurement units 401, 402, 403, 404, 405, 406 in PTD 1), which could become a cause of errors in test.

On the other hand, when a channel width of flow rate restriction unit 700' is increased in order to prevent pre-separation, a "clogging phenomenon" that a narrow portion 423' of hemocyte separation unit 420' is filled with whole blood 600' before the whole blood reaches a bottom portion of hemocyte separation unit 420', which blocks exhaust of air in hemocyte separation unit 420', and thus hemocyte separation unit 420' is not filled with whole blood 600', tends to occur. When such a clogging phenomenon occurs as well, a necessary amount of plasma component cannot be obtained, which could be a cause of errors in test.

Then, an object of the present invention is to provide a microchip (such as a blood test microchip) which includes a separation unit for separating a first component (such as a plasma component) and a second component (such as a hemocyte component) in a specimen (such as whole blood) containing the first component and the second component different in specific gravity from each other through centrifugation and is capable of reliably separating and extracting the first component in an amount necessary for fluid treatment within the microchip and hence accurately and reliably testing or analyzing the extracted first component.

Solution to Problem

The present invention provides a microchip including a first substrate; a second substrate stacked on the first substrate and having a groove on a substrate surface; a fluid circuit including a space defined by the groove and a surface of the first substrate on a side of the second substrate; and a specimen inlet for introducing in the fluid circuit, a specimen containing a first component and a second component different in specific gravity from each other. The fluid circuit includes a specimen measurement unit connected to the specimen inlet and having a prescribed volume for measuring the specimen introduced through the specimen inlet and a separation unit which is a site connected to the specimen measurement unit and having a capacity capable of storing a total amount of the measured specimen, for storing the total amount of the measured specimen and separating the first component and the second component in the stored specimen from each other.

The separation unit can be such a structure as including an opening for accepting the measured specimen, a first component storage unit for storing the separated first component, and a second component storage unit for storing the separated second component in this order. Preferably, a volume of the first component storage unit is greater than a volume of the measured specimen.

The microchip according to the present invention may be a microchip including a first substrate; a second substrate stacked on the first substrate and having a groove on each of opposing surfaces of the substrate; and a third substrate stacked on the second substrate. In this case, the fluid circuit includes a first fluid circuit consisting of a space defined by a surface of the first substrate on the side of the second substrate and a groove provided on a surface of the second substrate on a side of the first substrate and a second fluid circuit consisting of a space defined by a surface of the third substrate on a side of the second substrate and a groove provided on a surface of the second substrate on a side of the third substrate. Such a microchip having fluid circuits in two layers can be constructed, for example, such that the first fluid circuit has the specimen measurement unit and the second fluid circuit has the separation unit.

Advantageous Effects of Invention

According to the microchip of the present invention, a specimen measurement unit for measuring a prescribed amount of specimen is provided in a stage preceding a separation unit for separating a first component and a second component in the specimen from each other (that is, upstream in a direction of movement of the specimen in a fluid circuit) and the separation unit has a capacity capable of storing a total amount of the measured specimen. Therefore, even if pre-separation as described above should occur, fluctuation in content of a component in the specimen stored in the separation unit does not occur, the first component in an amount necessary for fluid treatment within the microchip can reliably be separated and extracted, and hence the extracted first component can accurately and reliably be tested or analyzed.

DESCRIPTION OF EMBODIMENTS

Figure 1:
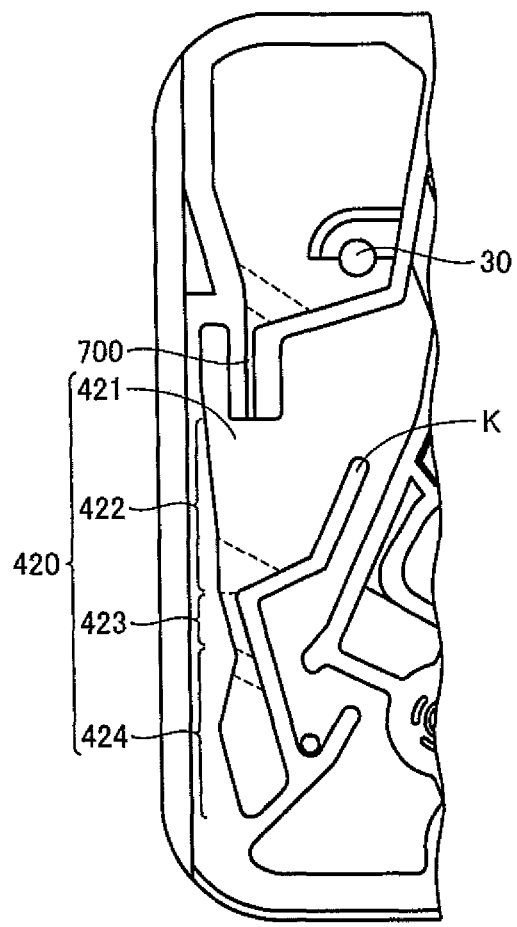
FIG. 1 is a plan view showing in a partially enlarged manner, one example of a second substrate forming a microchip according to the present invention.

A microchip according to the present invention is a chip capable of various types of chemical synthesis, tests or analysis, and the like with the use of a fluid circuit therein, and it is constructed to include at least a first substrate and a second substrate stacked on the first substrate and having a groove on a substrate surface. The fluid circuit of the microchip includes a space defined by the groove above and a surface of the first substrate on a side of the second substrate. A size of the microchip is not particularly limited, and it can be, for example, approximately from several cm to 10 cm long in horizontal and vertical directions and approximately from several mm to several cm thick.

Alternatively, the microchip according to the present invention may include a first substrate, a second substrate stacked on the first substrate and having a groove on each of opposing surfaces of the substrate, and a third substrate stacked on the second substrate. In this case, the fluid circuit has a two-layered structure consisting of a first fluid circuit and a second fluid circuit. The first fluid circuit is composed of a space defined by a surface of the first substrate on a side of the second substrate and a groove provided on a surface of the second substrate on a side of the first substrate. The second fluid circuit is composed of a space defined by a surface of the third substrate on a side of the second substrate and a groove provided on a surface of the second substrate on a side of the third substrate. As used herein, "two-layered" means that fluid circuits are provided at two different positions in a thickness direction of the microchip. Such fluid circuits in two layers may be connected to each other via a through hole penetrating the second substrate in the thickness direction.

The fluid circuits have a two-layered structure so that integration and higher density of fluid circuits can be achieved and thus a microchip capable of performing more complicated fluid treatment can be obtained. Moreover, a substrate area (microchip area) can be reduced. Thus, flatness of each substrate at the time of bonding of the substrates to each other can more readily be ensured and uniformity in pressure across the entire substrate at the time of bonding of the substrates to each other can more readily be achieved, so that insufficient adhesion between the substrates can be prevented.

A method of bonding substrates to each other is not particularly limited. For example, a method of fusing at least one of substrate bonding faces of the substrates to be bonded for welding (a welding method), a method of adhesion using an adhesive, and the like can be exemplified. The welding method includes a method of heating a substrate for welding, a method of emitting light such as laser beams to effect welding by heat generated during light absorption (laser welding), a method of welding with the use of ultrasonic waves, and the like can be exemplified. Among these, the laser welding method is preferably employed.

A material for each substrate above forming the microchip of the present invention is not particularly restricted, and an organic material such as polyethylene terephthalate (PET), polyethylenenaphthalate (PEN), polybutylene terephthalate (PBT), polymethylmethacrylate (PMMA), polycarbonate (PC), polystyrene (PS), polypropylene (PP), polyethylene (PE), polyarylate resin (PAR), acrylonitrile butadiene styrene resin (ABS), styrene-butadiene resin (styrene-butadiene copolymer), polyvinyl chloride resin (PVC), polymethyl pentene resin (PMP), polybutadiene resin (PBD), biodegradable polymer (BP), cyeloolefin polymer (COP), polydimethylsiloxane (PDMS), polyacetal (POM), and polyamide (PA), as well as an inorganic material such as silicon, glass, and quartz, and the like can be employed. Among these, in consideration of ease in formation of a fluid circuit, a resin is preferably employed and a styrene-based resin such as a styrene-butadiene copolymer is more preferably employed. Since the styrene-butadiene resin has favorable transparency based on styrene and favorable viscosity based on butadiene together, the resin can readily be detached from a mold without breakage while maintaining its shape even in the case where an area of contact between the resin and the mold is extremely large in order to form minute patterns.

In a case where a microchip is constituted of a first substrate and a second substrate having a groove on a substrate surface, the second substrate includes a site irradiated with detection light during optical measurement and hence a transparent substrate is preferably adopted for the second substrate. Though the first substrate may be a transparent substrate or an opaque substrate, an opaque substrate is preferably adopted for the first substrate because optical absorptance can be increased in performing laser welding and a black substrate prepared by forming the substrate from a resin and adding a black pigment such as carbon black to the resin is more preferably adopted for the first substrate.

In a case where a microchip is constituted of a first substrate, a second substrate having a groove on each of opposing surfaces of the substrate, and a third substrate, from a point of view of efficiency in laser welding, for the second substrate, an opaque substrate is preferably employed and a black substrate is more preferably employed. On the other hand, a transparent substrate is preferably adopted for the first and third substrates in order to construct a detection unit. By employing a transparent substrate for the first and third substrates, a detection unit (an optical measurement cuvette) can be formed from a through hole provided in the second substrate and the transparent first and third substrates, so that such optical measurement as irradiation of the detection unit with light from a direction substantially perpendicular to the microchip surface to thereby detect intensity of transmitting light (transmissivity) or the like can be conducted.

A method of forming grooves (pattern grooves) forming a fluid circuit at the surface of the second substrate is not particularly restricted, and injection molding employing a mold having a transfer structure, imprinting, and the like can be exemplified. In the case where a substrate is formed of an inorganic material, an etching method or the like can be employed. A shape of a groove is determined for obtaining an appropriate fluid circuit structure.

In the microchip according to the present invention, the fluid circuit includes various sites arranged at appropriate positions therein such that a liquid (a specimen, a specific component in the specimen, a liquid reagent, a mixture or a reactant of two or more types thereof, and the like) within the fluid circuit can be subjected to appropriate fluid treatment, and these sites are appropriately connected through minute channels.

In the microchip according to the present invention, the fluid circuit includes at least a specimen measurement unit having a prescribed volume for measuring a specimen and a separation unit for separating a component in the specimen. As used herein, the "specimen" refers to a substance introduced in the fluid circuit, which is to be subjected to test, analysis, or the like by the microchip, and it is represented, for example, by whole blood. The specimen contains a first component and a second component different in specific gravity from each other, and the first component which is extracted from the specimen and is to be subjected to fluid treatment for test, analysis, or the like is normally smaller in specific gravity than the second component. The specimen is introduced into the fluid circuit through the specimen inlet consisting of a through hole penetrating the first substrate (or the third substrate) in a direction of thickness and connected to the fluid circuit.

The specimen measurement unit is a site connected to the specimen inlet, for measuring the specimen introduced through the specimen inlet. In addition, the separation unit is a site connected to the specimen measurement unit, for storing the total amount of the measured specimen and separating the first component and the second component in the stored specimen from each other. Namely, these sites are connected in series in the order of the specimen inlet→the specimen measurement unit→the separation unit, and the specimen moves through the sites in this order as centrifugal force in an appropriate direction is applied to the microchip.

By providing the specimen measurement unit and the separation unit in arrangement as above, even in a case where a flow rate restriction unit as described above is provided between the specimen measurement unit and the separation unit, the first component in an amount necessary for fluid treatment within the microchip can reliably be separated and extracted. Namely, in the microchip according to the present invention having the specimen inlet, the specimen measurement unit, and the separation unit in this order, the specimen introduced through the specimen inlet is stored in the specimen measurement unit having a prescribed volume as a result of application of centrifugal force and the prescribed amount of specimen is measured [an excess of the specimen is overspilt and stored in an overflow liquid storage unit (a waste reservoir)]. The "prescribed amount" refers to at least an amount containing the first component necessary for fluid treatment within the microchip.

Then, in a case where the flow rate restriction unit is present between the specimen measurement unit and the separation unit, the measured specimen is introduced in the separation unit through this flow rate restriction unit. Here, since the separation unit has a capacity capable of storing the total amount of the measured specimen, the total amount of the measured specimen is stored in the separation unit. Therefore, even when "pre-separation" as described above occurs in the flow rate restriction unit, component composition of the specimen stored in the separation unit is the same as that of the specimen introduced through the specimen inlet and fluctuation in content of the component does not occur. Therefore, since the separation unit stores the specimen in at least an amount containing the first component necessary for fluid treatment within the microchip, the first component in an amount necessary for fluid treatment within the microchip can reliably be separated and extracted by centrifuging the specimen.

Though it is not required to provide the flow rate restriction unit, the flow rate restriction unit is preferably provided in order to reliably guide the measured specimen to the separation unit.

FIG. 1 is a plan view showing in a partially enlarge manner, one example of the second substrate forming the microchip according to the present invention, and shows a part of the second substrate forming a microchip 100 according to a first embodiment which will be described later. As will be described later, this microchip 100 has fluid circuits in two layers and FIG. 1 shows a part of a lower fluid circuit (a second fluid circuit). Referring to FIG. 1, microchip 100 includes a flow rate restriction unit 700 and a separation unit 420 as parts of the lower fluid circuit. As illustrated, separation unit 420 preferably has a structure including an opening 421 provided directly under an end portion of flow rate restriction unit 700 for accepting the specimen, a first component storage unit 422 for storing the first component separated by centrifugation, and a second component storage unit 424 for storing the separated second component in this order. First component storage unit 422 and second component storage unit 424 are connected to each other through a narrow portion 423 composed of a space relatively small in capacity (narrow in width). Separation unit 420 is designed such that an interface between the first component and the second component is located within this narrow portion 423. The first component stored in first component storage unit 422 as a result of centrifugation is separated and extracted from a liquid (mainly composed of the second component) stored in narrow portion 423 and second component storage unit 424 by applying centrifugal force rightward in FIG. 1 to the microchip in a next process. It is noted that flow rate restriction unit 700 and the specimen measurement unit not shown in FIG. 1 (which is arranged within an upper fluid circuit) are connected to each other through a through hole 30.

In the microchip constructed as above as well, occurrence of the "clogging phenomenon" as described above cannot completely be eliminated due to influence by a channel width or the like of flow rate restriction unit 700. Therefore, a volume of first component storage unit 422 in separation unit 420 is preferably greater than a volume of the measured specimen (that is, a volume of the specimen measurement unit) such that a necessary amount of the first component can reliably be obtained in spite of occurrence of the clogging phenomenon. Thus, even when the clogging phenomenon occurs, first component storage unit 422 alone can store the total amount of the measured specimen. Therefore, such a defect that the specimen is overspilt from separation unit 420 due to the clogging phenomenon and an amount of the specimen stored in separation unit 420 is insufficient can be prevented. A volume of first component storage unit 422 can readily be adjusted by adjusting a depth of a groove in that region or a length of a wall K delimiting first component storage unit 422.

The microchip according to the present invention can suitably be employed, for example, as a blood test microchip, and in this case, the separation unit can be made use of as a hemocyte separation unit for separating and removing a hemocyte component (a second component) from the whole blood introduced into the fluid circuit and extracting a plasma component (a first component). The extracted plasma component is subjected to necessary fluid treatment within the fluid circuit and to test or analysis.

The fluid circuit may have sites other than the specimen measurement unit and the separation unit above. Other sites are not particularly limited, and a reagent receptacle unit for holding a liquid reagent, a first component measurement unit for measuring the extracted first component (such as a plasma component), a reagent measurement unit for measuring the liquid reagent, a mixing unit for mixing the measured liquid reagent and the measured first component with each other, a detection unit for testing or analyzing the obtained liquid mixture (for example, detecting a specific component in the liquid mixture), and the like can be exemplified. One site or two or more sites may be provided. In addition, the microchip according to the present invention may have all of these exemplified sites, or it does not have to have one or more of them. Furthermore, the microchip may have a site other than these exemplified sites.

It is noted that the "liquid reagent" refers to a reagent for treating a specimen (first component) to be subjected to test or analysis conducted by the microchip or for being mixed with or reacted to the specimen, and it is normally contained in the reagent receptacle unit in the fluid circuit in advance prior to use of the microchip.

In a case where the fluid circuit has a two-layered structure, each site may be arranged within any of the first fluid circuit and the second fluid circuit, however, from a point of view of higher integration and higher density of fluid circuits, the separation unit is preferably arranged within the second fluid circuit when the specimen measurement unit is arranged within the first fluid circuit.

In the case where the microchip according to the present invention has a reagent receptacle unit, a reagent inlet that is a through hole penetrating to the internal reagent receptacle unit is generally provided on a microchip surface (first or third substrate surface). Such a microchip generally has a liquid reagent injected through the reagent inlet, and then a label or seal for sealing the reagent inlet is attached to the microchip surface for use.

Various fluid treatments within the fluid circuit such as measurement of a specimen, extraction of a first component from the specimen, measurement of the first component and a liquid reagent, mixing of the first component and the liquid reagent with each other, and introduction of the obtained liquid mixture into the detection unit can be performed by successively applying centrifugal force in an appropriate direction to the microchip. Centrifugal force can be applied to the microchip in such a manner that the microchip is mounted on an apparatus capable of applying centrifugal force (a centrifuge). The centrifuge can include a freely rotatable rotor and a freely rotatable stage arranged on the rotor. By mounting the microchip on the stage and setting an arbitrary angle of the microchip with respect to the rotor through turning of the stage, centrifugal force in an arbitrary direction can be applied to the microchip.

The liquid mixture finally obtained as a result of mixing of the first component and the liquid reagent with each other is not particularly limited, and for example, such optical measurement as a method of detecting intensity of transmitting light (transmissivity) by irradiating the detection unit storing the liquid mixture with light, a method of measuring an absorption spectrum of the liquid mixture held in the detection unit, and the like is conducted for test or analysis.

The present invention will be described hereinafter in detail with reference to embodiments.

First Embodiment

Figure 2:
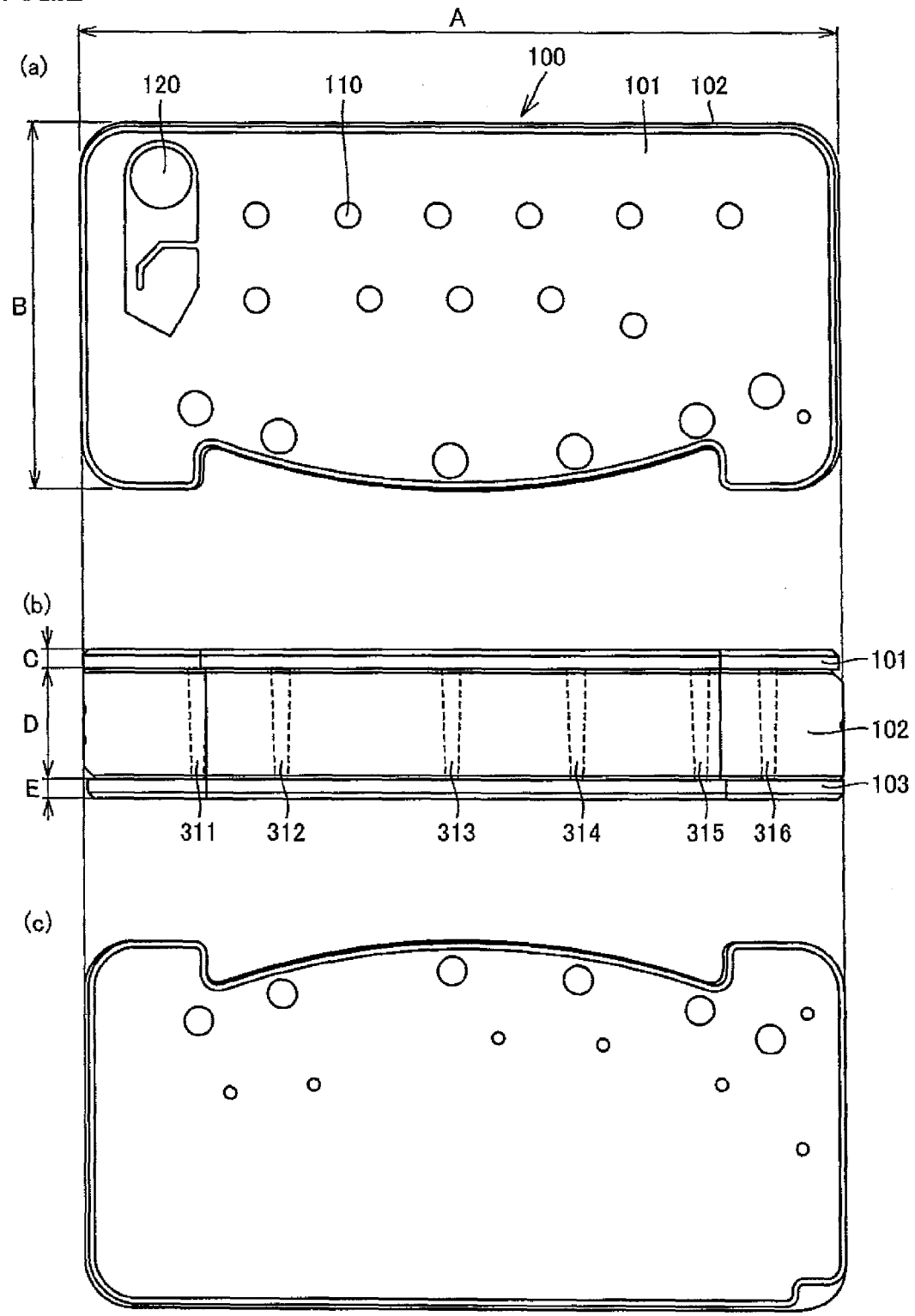
FIG. 2 is a diagram showing an outer shape of one example of the microchip according to the present invention.

FIG. 2 is a diagram of an outer shape showing one example of the microchip according to the present invention. FIG. 2 (a) is a top view, FIG. 2 (b) is a side view, and FIG. 2 (c) is a bottom view. Microchip 100 shown in FIG. 2 is formed by bonding together a first substrate 101 that is a transparent substrate, a second substrate 102 that is a black substrate, and a third substrate 103 that is a transparent substrate, in this order [refer to FIG. 2 (b)]. Vertical and lateral lengths of these substrates are not particularly limited, and the lengths are approximately 62 mm in the lateral direction (A in FIG. 2) and approximately 30 mm in the vertical direction (B in FIG. 2) in the present embodiment. In the present embodiment, thicknesses of first substrate 101, second substrate 102, and third substrate 103 (C, D, and E in FIG. 2, respectively) are set to approximately 1.6 mm, approximately 9 mm, and approximately 1.6 mm, respectively. It is noted that the dimension is not limited thereto.

First substrate 101 includes a reagent inlet 110 (a total of 11 inlets in the present embodiment) penetrating in the thickness direction and a specimen inlet 120 for introducing a specimen (for example, whole blood) into the fluid circuit of the microchip. Microchip 100 in the present embodiment generally has a liquid reagent injected through liquid reagent inlet 110, which is thereafter sealed by a label for sealing or the like to be presented for actual use.

Second substrate 102 includes grooves formed on opposing surfaces thereof and a plurality of through holes penetrating in the thickness direction. By bonding first substrate 101 and third substrate 103 thereto, fluid circuits in two layers are formed in the microchip. Hereinafter, the fluid circuit constituted of the surface of first substrate 101 on the side of second substrate 102 and a groove provided on the surface of second substrate 102 on the side of first substrate 101 is referred to as a "first fluid circuit," and the fluid circuit constituted of the surface of third substrate 103 on the side of second substrate 102 and a groove provided on the surface of second substrate 102 on the side of third substrate 103 is referred to as a "second fluid circuit." These two fluid circuits are coupled to each other via a through hole formed in second substrate 102 and penetrating in the thickness direction. A construction of the fluid circuits (grooves) formed on respective opposing surfaces of second substrate 102 will be described in detail hereinafter.

Figure 3:
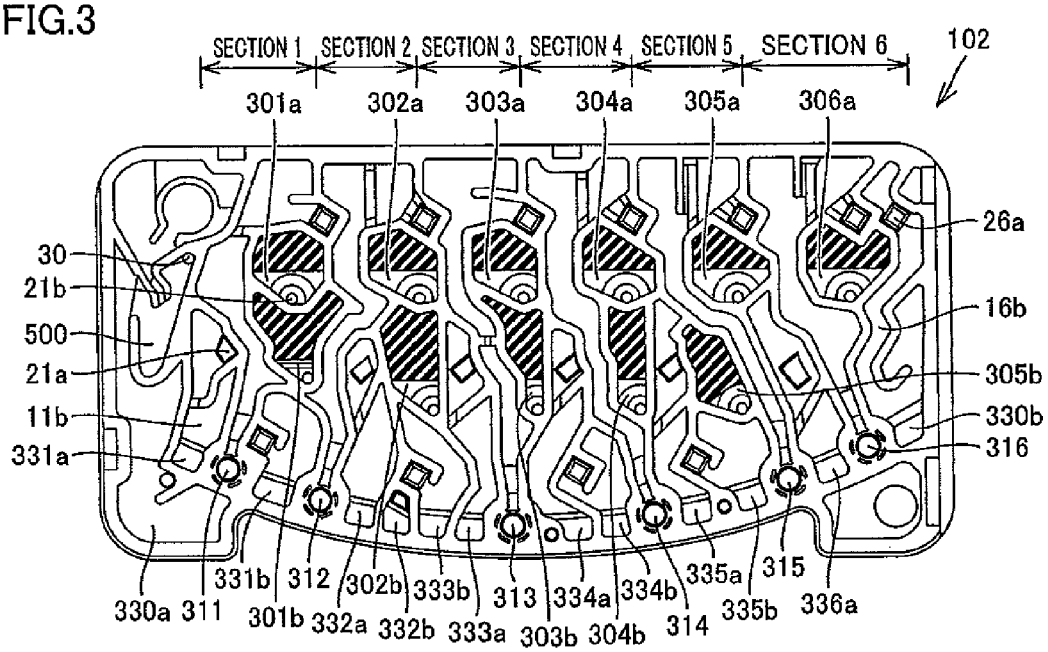
FIG. 3 is a top view showing one example of the second substrate forming the microchip according to the present invention.
Figure 4:
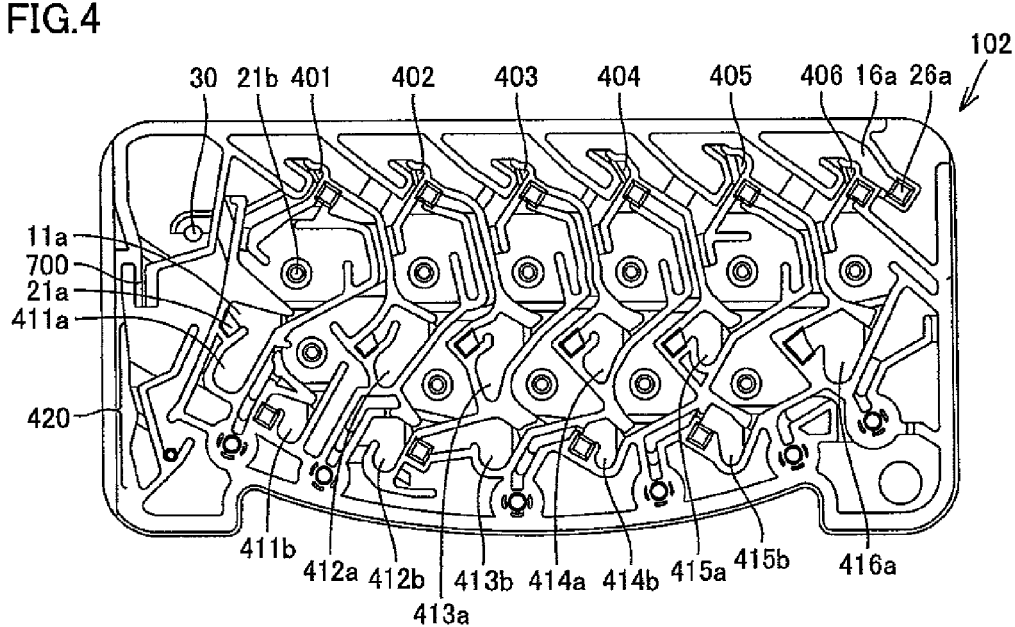
FIG. 4 is a bottom view showing one example of the second substrate forming the microchip according to the present invention.

FIGS. 3 and 4 show a top view and a bottom view, respectively, of second substrate 102, the former showing an upper fluid circuit (the first fluid circuit) and the latter showing a lower fluid circuit (the second fluid circuit), of second substrate 102. In FIG. 4, the lower fluid circuit of second substrate 102 is shown in a mirror-reversed manner for the sake of clear understanding of correspondence with the upper fluid circuit shown in FIG. 3. Microchip 100 in the present embodiment is a multi-test chip that allows test or analysis of six items for one specimen. The fluid circuit is divided into six sections (sections 1-6 in FIG. 3) to allow test or analysis of six items [it is noted that these sections are connected with each other at a region where a first component measurement unit is located (an upper region of the lower fluid circuit)]. Thus, according to the present embodiment, since fluid circuits in two layers are provided, integration and higher density of the fluid circuits can be achieved so that a microchip capable of testing or analyzing multiple items in spite of its relatively small area can be provided.

Each section above is provided with one or two reagent receptacle unit(s) within the first fluid circuit (upper fluid circuit), in which a liquid reagent is contained (a total of eleven reagent receptacle units 301*a*, 301*b*, 302*a*, 302*b*, 303*a*, 303*b*, 304*a*, 304*b*, 305*a*, 305*b*, and 306*a* in FIG. 3). The specimen introduced through specimen inlet 120 in FIG. 2 is measured, then it has a hemocyte component separated and removed therefrom, and it is thereafter distributed to each section and measured. Then, the specimen is mixed with one or two type(s) of liquid reagent(s) in each section that is/are measured separately, and then introduced into detection units 311, 312, 313, 314, 315, and 316. The liquid mixture introduced into each detection unit in each section is subjected to optical measurement such as irradiation of the detection unit with light from a direction substantially perpendicular to the surface of the microchip and measurement of transmissivity of the transmitted light, and a specific component in the liquid mixture or the like is detected. A series of these fluid treatments is effected by applying centrifugal force to the microchip in an appropriate direction so that a liquid reagent, a specimen, a first component, or a liquid mixture of the first component and the liquid reagent is moved in an appropriate order to each site in the fluid circuits in two layers provided in each section. Centrifugal force can be applied to the microchip, for example, by placing the microchip in the centrifuge described above.

Each reagent receptacle unit is connected to the reagent measurement unit through the through hole penetrating second substrate 102. For example, reagent receptacle unit 301*a* (see FIG. 3) and reagent measurement unit 411*a* (see FIG. 4) in section 1 are connected to each other via a through hole 21*b*. This is also the case with other reagent receptacle units and reagent measurement units. Thus, by providing the fluid circuits in two layers and coupling these to each other through a through hole, even in a microchip relatively small in area, the fluid circuit can efficiently be made use of through movement between the first fluid circuit and the second fluid circuit, and complicated liquid movement or the like can also be controlled.

In addition, each section above is provided with a first component measurement unit for measuring the first component separated from the specimen (a total of six specimen measurement units 401, 402, 403, 404, 405, and 406 in FIG. 4) and a reagent measurement unit for measuring a liquid reagent (a total of eleven reagent measurement units 411*a*, 411*b*, 412*a*, 412*b*, 413*a*, 413*b*, 414*a*, 414*b*, 415*a*, 415*b*, and 416*a* in FIG. 4), within the second fluid circuit (lower fluid circuit). The first component measurement units are connected in series through a channel (see FIG. 4).

Moreover, microchip 100 in the present embodiment includes a specimen measurement unit 500 (see FIG. 3) for measuring the specimen introduced into the microchip, flow rate restriction unit 700 (see FIG. 4), and separation unit 420 (see FIG. 4) for separating a second component from the measured specimen and extracting the first component (a component to be mixed with the liquid reagent). Separation between the first component and the second component is achieved by centrifugation. Specimen measurement unit 500 and flow rate restriction unit 700 are connected to each other through through hole 30.

As shown in FIG. 3, microchip 100 includes overflow liquid storage units 330*a*, 330*b* for storing a specimen or a first component overspilt from the specimen measurement unit and the first component measurement unit during measurement and overflow reagent storage units 331*a*, 331*b*, 332*a*, 332*b*, 333*a*, 333*b*, 334*a*, 334*b*, 335*a*, 335*b*, and 336*a* for storing a liquid reagent overspilt from the reagent measurement unit during measurement. Overflow liquid storage unit 330*b* is connected to first component measurement unit 406 via a channel 16*a* (see FIG. 4), a through hole 26*a* penetrating in the thickness direction, and a channel 16*b* (see FIG. 3). Furthermore, each overflow reagent storage unit is connected to a corresponding reagent measurement unit via a channel and a through hole. In section 1, for example, reagent measurement unit 411*a* for measuring the liquid reagent stored in reagent receptacle unit 301*a* is connected to overflow reagent storage unit 331*a* (see FIG. 3) for storing the overspilt liquid reagent via a channel 11*a* (see FIG. 4), a through hole 21*a* penetrating in the thickness direction, and a channel 11*b* (see FIG. 3). This is also the case with other overflow reagent storage units.

By providing the microchip with overflow liquid storage units and overflow reagent storage units (which hereinafter may also collectively be referred to as an overflow storage unit) and detecting absence or presence of an overspilt substance in the overflow storage unit, a specimen, a first component, or a liquid reagent is reliably transferred to the measurement unit by means of a centrifugal operation, and whether or not the measurement unit is filled with a measurement target can readily be checked. Namely, sensing of presence of the overspilt substance in the overflow storage unit assures that the specimen, the first component, or the liquid reagent was accurately measured by the measurement unit. Accordingly, reliability of test or analysis can be improved.

As a method of sensing whether or not an overspilt substance is present in an overflow storage unit, for example, a method of irradiating the overflow storage unit with light from the side of first substrate 101 that is a transparent substrate and measuring intensity of reflected light can preferably be employed. The light to be employed is not particularly restricted, and it may be, for example, monochromatic light (for example, laser beam) having a wavelength approximately from 400 to 1000 nm or mixed light such as white light. Intensity of reflected light can be measured, for example, by using a commercially available reflection sensor.

In the method of sensing absence or presence of an overspilt substance through measurement of intensity of reflected light, basically, absence or presence of an overspilt substance is sensed by finding a ratio of intensity in such a manner as finding a ratio of intensity of reflected light obtained by irradiating the overflow storage unit with light from the side of first substrate 101 before an overspilt substance is introduced in the overflow storage unit to intensity of reflected light obtained by irradiating the overflow storage unit with light from the first substrate side after a measurement target is introduced into the measurement unit. Namely, when the ratio (reflected light intensity after introduction/reflected light intensity before introduction) is lower than 1 (a case where intensity of reflected light after introduction is lower), it is determined that an overspilt substance is present in the overflow storage unit. It is noted that measurement of intensity of reflected light before introduction of an overspilt substance can be skipped in the case where manufacturing variation among microchips is less and hence intensity of reflected light before introduction of an overspilt substance can be regarded as substantially constant among microchips.

Thus, microchip 100 in the present embodiment has the total of eleven overflow reagent storage units corresponding to respective liquid reagents and two overflow liquid storage units, which are all arranged in the first fluid circuit (upper fluid circuit) (refer to FIG. 3). By arranging all overflow storage units in one fluid circuit, the microchip does not have to be turned over at the time of measurement of reflected light intensity, thereby allowing simplified and rapid sensing of absence or presence of an overspilt substance in all the overflow storage units. Moreover, these overflow storage units, among others the overflow reagent storage unit and overflow liquid storage unit 330b, are preferably arranged on the circumference of the same circle in one fluid circuit formed in the surface of the second substrate (see FIG. 3, in microchip 100, the total of 11 overflow reagent storage units and one overflow liquid storage unit 330b are thus arranged). This circle is preferably a circle around the revolution center in causing the microchip to revolve in order to provide the microchip with centrifugal force. More specifically, since a microchip is generally mounted on a rotatable circular stage of a centrifuge and centrifugal force is applied thereto, it can be said that the circle with the center of revolution being defined as the center is a circle with the center of rotation of the circular stage being defined as the center. By thus arranging the overflow storage units on the circumference of the same circle, reflected light intensity can be measured by emitting light from a fixed light source (or an apparatus having a light source and reflected light intensity measurement means integrally formed) while the circular stage on which the microchip is mounted is rotated to sequentially arrange overflow storage units on an optical axis of emitted light. Thus, measurement of reflected light intensity can readily and rapidly be conducted.

An example of fluid treatment with the use of microchip 100 in the present embodiment will now be described with reference to FIGS. 5 to 13. FIGS. 5 to 13 are diagrams showing a state of a liquid (a specimen, a first component, a liquid reagent, and a liquid mixture of the first component and the liquid reagent) at the top face of second substrate 102 (the surface on the side of the first substrate) and a state of a liquid at the bottom face of second substrate 102 (the surface on the side of the third substrate) during each process in the fluid treatment. In each figure, (a) is a diagram showing a state of the liquid at the top face of the second substrate (first fluid circuit) whereas (b) is a diagram showing a state of the liquid at the bottom face of the second substrate (second fluid circuit). It is noted that, in (b) of FIGS. 5 to 13, as in FIG. 4, the lower fluid circuit of second substrate 102 is shown in a mirror-reversed manner for clear understanding of correspondence with the upper fluid circuit shown in (a) of FIGS. 5 to 13. Although description only of fluid treatment in the fluid circuit in section 1 will be given in the description below, a similar treatment is carried out also in other sections, which can clearly be understood by referring to the drawings. Further, although description of a case where a specimen is whole blood will be given by way of example, a type of a specimen is not limited thereto.

(1) Whole Blood Measurement and Liquid Reagent Measurement Process

Figure 5:
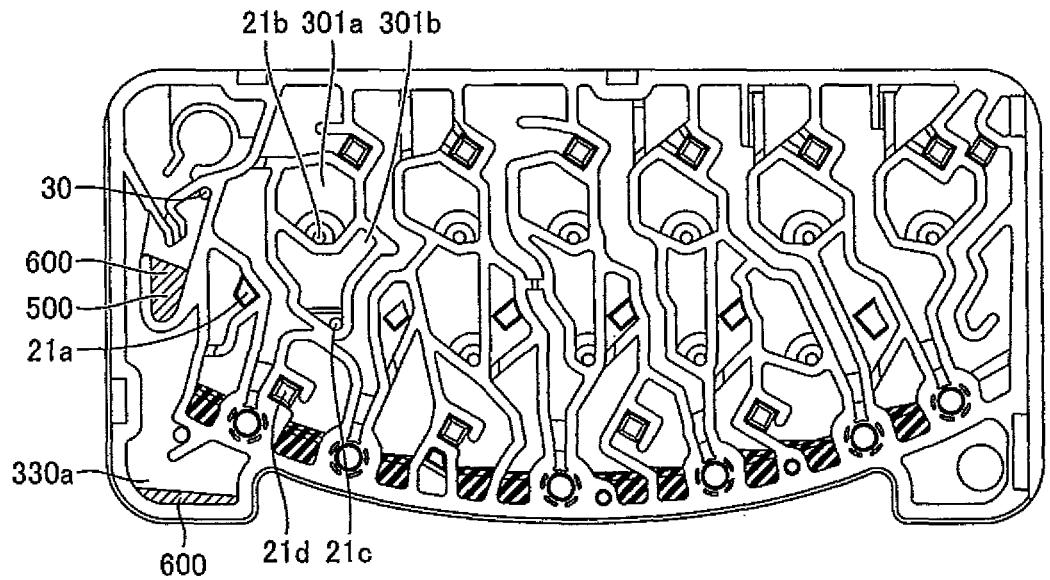
FIG. 5 is a diagram showing a state of a liquid at a top face of the second substrate (a surface on a side of a first substrate) and a state of a liquid at a bottom face thereof (a surface on a side of a third substrate) in a whole blood measurement and reagent measurement process in fluid treatment using the microchip shown in FIGS. 2 to 4.
Figure 5:
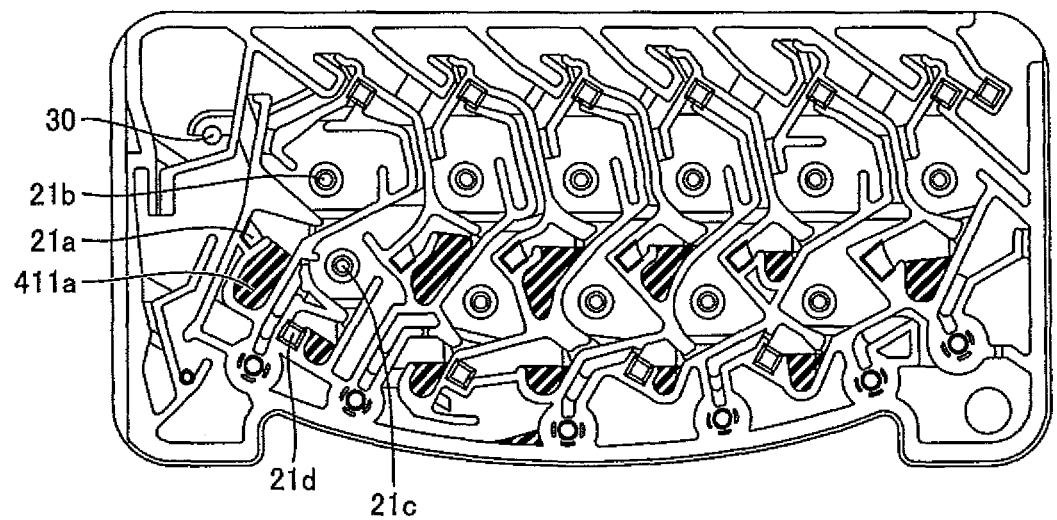
Figure 6:
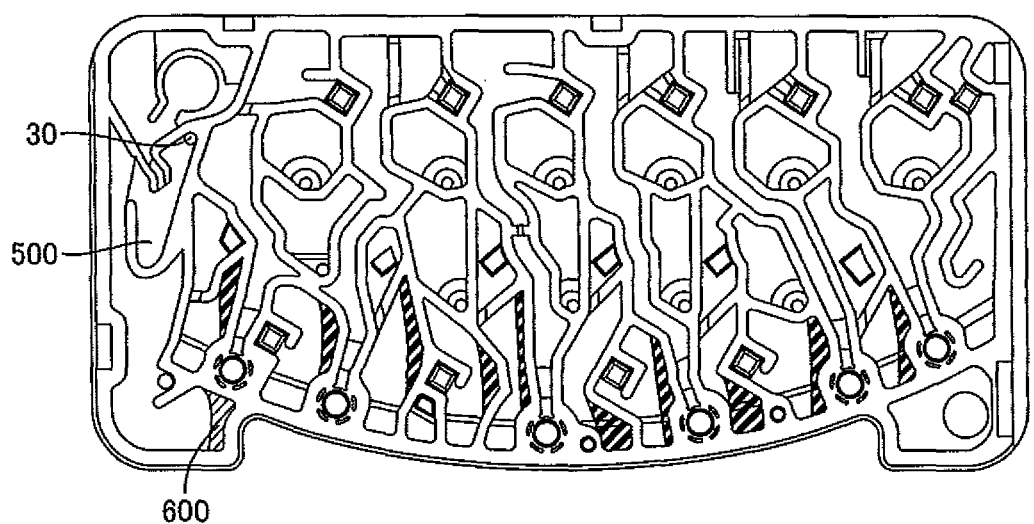
FIG. 6 is a diagram showing a state of a liquid at the top face of the second substrate (the surface on the side of the first substrate) and a state of a liquid at the bottom face thereof (the surface on the side of the third substrate) in a whole blood movement process in the fluid treatment using the microchip shown in FIGS. 2 to 4.
Figure 6:
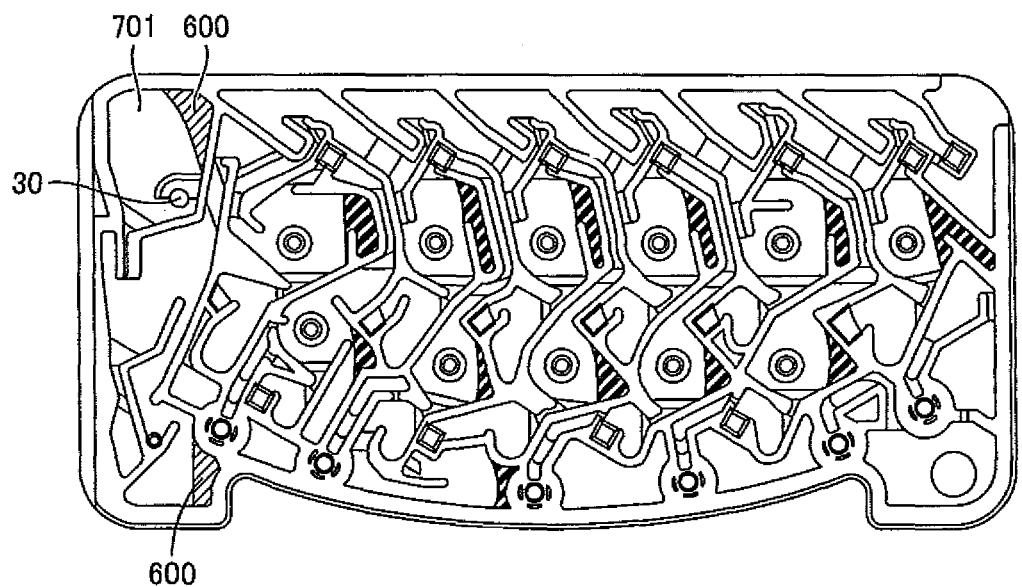
Figure 7:
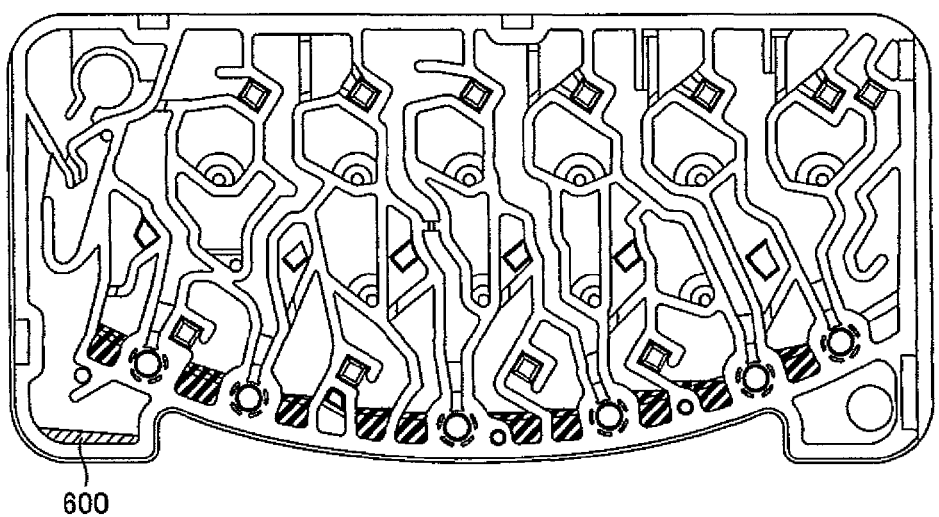
FIG. 7 is a diagram showing a state of a liquid at the top face of the second substrate (the surface on the side of the first substrate) and a state of a liquid at the bottom face thereof (the surface on the side of the third substrate) in a hemocyte separation process in the fluid treatment using the microchip shown in FIGS. 2 to 4.
Figure 7:
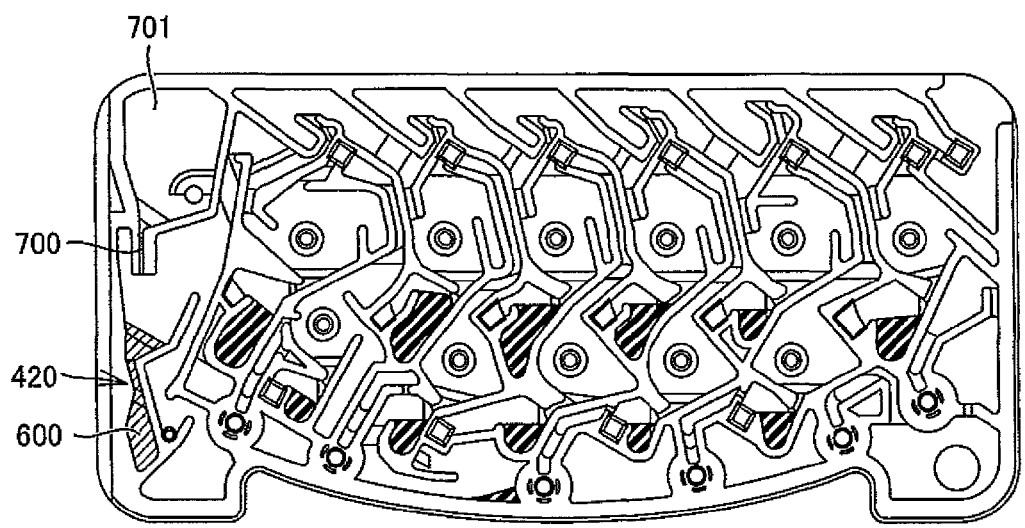
Figure 8:
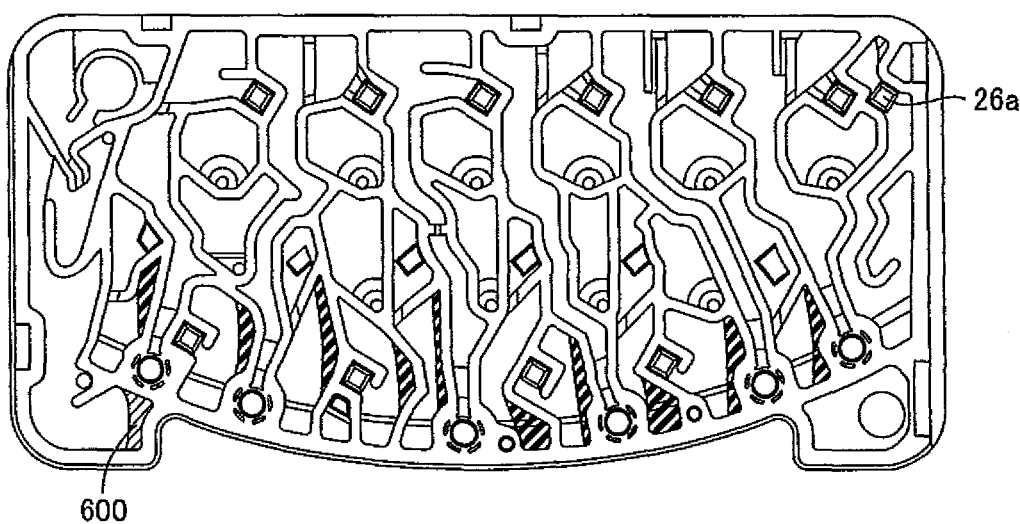
FIG. 8 is a diagram showing a state of a liquid at the top face of the second substrate (the surface on the side of the first substrate) and a state of a liquid at the bottom face thereof the surface on the side of the third substrate) in a plasma component measurement process in the fluid treatment using the microchip shown in FIGS. 2 to 4.
Figure 8:
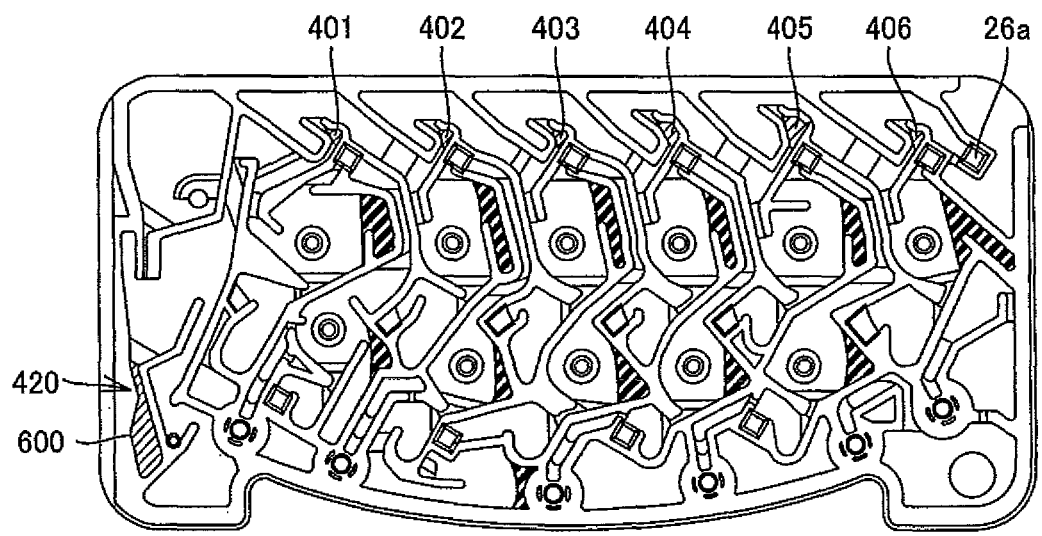
Figure 9:
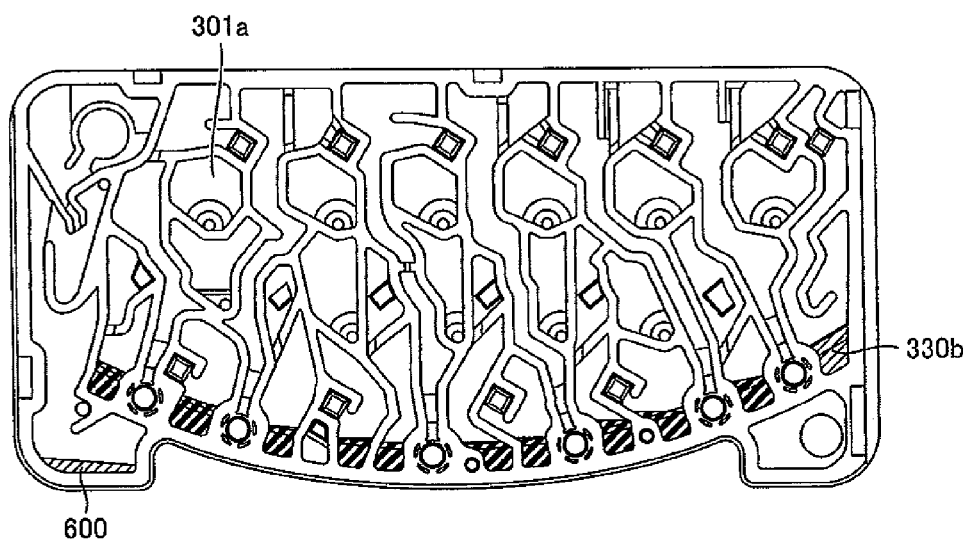
FIG. 9 is a diagram showing a state of a liquid at the top face of the second substrate (the surface on the side of the first substrate) and a state of a liquid at the bottom face thereof (the surface on the side of the third substrate) in a first step of a first mixing process in the fluid treatment using the microchip shown in FIGS. 2 to 4.
Figure 9:
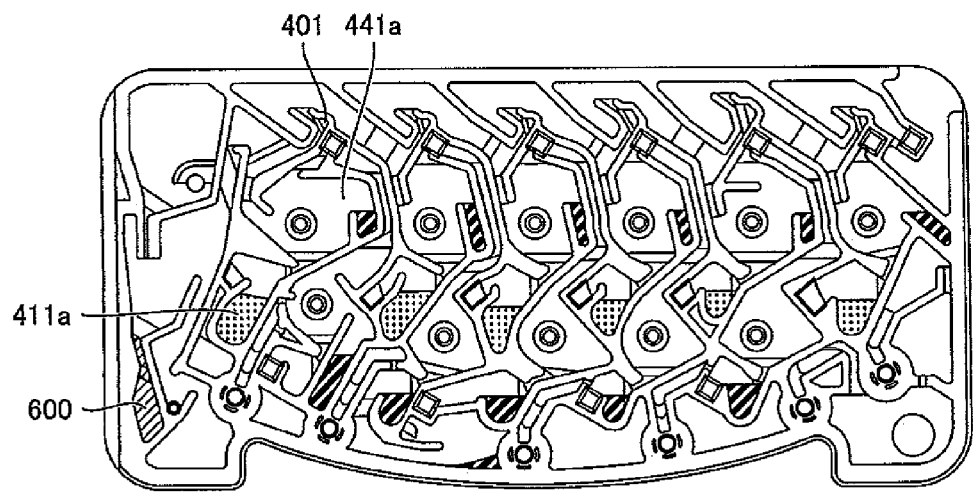

Initially, in the present process, centrifugal force is applied in a downward direction in FIG. 5 (hereinafter simply referred to downward, which is also the case with FIGS. 6 to FIG. 13 and is to also similarly be understood with regard to other directions) to microchip 100 in the state shown in FIGS. 3 and 4. Accordingly, whole blood 600 introduced through specimen inlet 120 (see FIG. 2) of first substrate 101 is introduced in specimen measurement unit 500 and measured. Whole blood 600 overspilt from specimen measurement unit 500 is stored in overflow liquid storage unit 330a [see FIG. 5 (a)]. In addition, as a result of application of this downward centrifugal force, the liquid reagent within liquid reagent receptacle units 301a, 301b passes through through holes 21b, 21c, to reach reagent measurement units 411a, 411b, respectively, and then it is measured [see FIG. 5 (b)]. The liquid reagent overspilt from each liquid reagent measurement unit passes through through holes 21a, 21d to be stored in overflow reagent storage units 331a, 331b in the fluid circuit on a top face side [see FIG. 5 (a)]. At this stage, a liquid reagent is present in all the overflow reagent storage units except for overflow reagent storage unit 332b in the case where there is no fault in liquid amount in connection with the liquid reagent. It is noted that presence of a liquid reagent may be checked by irradiating a reagent receptacle unit with light and measuring intensity of reflected light prior to the present process. In addition, by irradiating the reagent measurement unit, the mixing unit, and the detection unit with light and measuring intensity of reflected light at a stage prior to the whole blood measurement and liquid reagent measurement process, whether or not a liquid reagent or a specimen is present at these sites may also be checked.

(2) Whole Blood Movement Process

Then, rightward centrifugal force is applied. Thus, measured whole blood 600 in specimen measurement unit 500 passes through through hole 30 and moves to a stand-by portion 701 in the lower fluid circuit [see FIG. 6 (b)].

(3) Hemocyte Separation Process

Then, downward centrifugal force is applied. Thus, the total amount of measured whole blood 600 in stand-by portion 701 passes through flow rate restriction unit 700 and is introduced in separation unit 420 [see FIG. 7 (b)]. Whole blood 600 introduced in separation unit 420 is centrifuged in separation unit 420 and separated into a plasma component (upper layer) and a hemocyte component (lower layer). Each liquid reagent is again stored in the reagent measurement unit.

(4) Plasma Component Measurement Process

Then, rightward centrifugal force is applied. Thus, the plasma component within the first component storage unit separated in separation unit 420 is introduced into first component measurement unit 401 (also introduced simultaneously into first component measurement units 402, 403, 404, as well as into 405 and 406) for measurement [see FIG. 8 (b)]. The plasma component overspilt from the measurement unit moves into the upper fluid circuit via through hole 26a [see FIG. 8 (a)]. It is noted that, at this stage, presence of the plasma component in the first component measurement unit may be checked by irradiating each first component measurement unit with light and measuring intensity of reflected light.

(5) First Mixing Process

Then, downward centrifugal force is applied. Thus, the measured liquid reagent the liquid reagent held in reagent receptacle unit 301a) and the plasma component measured in first component measurement unit 401 are mixed in reagent measurement unit 411a [a first step of a first mixing process. See FIG. 9 (b)]. Here, a liquid reagent remains in mixing unit 441a in the lower fluid circuit. It is noted that presence of a liquid mixture in the reagent measurement unit may be checked at this stage by irradiating each reagent measurement unit with light and measuring intensity of reflected light. In addition, by measuring intensity of reflected light from overflow liquid storage unit 330b at this stage, such a defect as insufficient introduction of a specimen can promptly be sensed.

Figure 10:
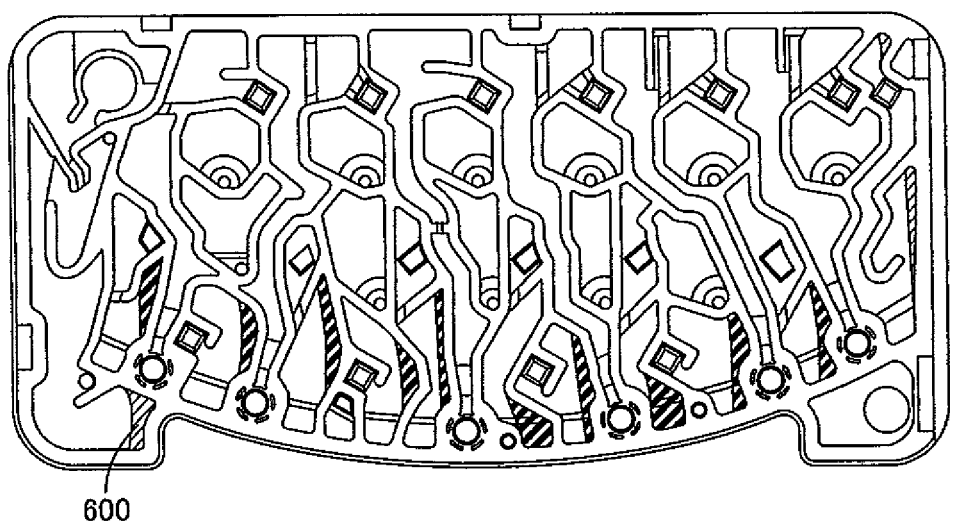
FIG. 10 is a diagram showing a state of a liquid at the top face of the second substrate (the surface on the side of the first substrate) and a state of a liquid at the bottom face thereof (the surface on the side of the third substrate) in a second step of the first mixing process in the fluid treatment using the microchip shown in FIGS. 2 to 4.
Figure 10:
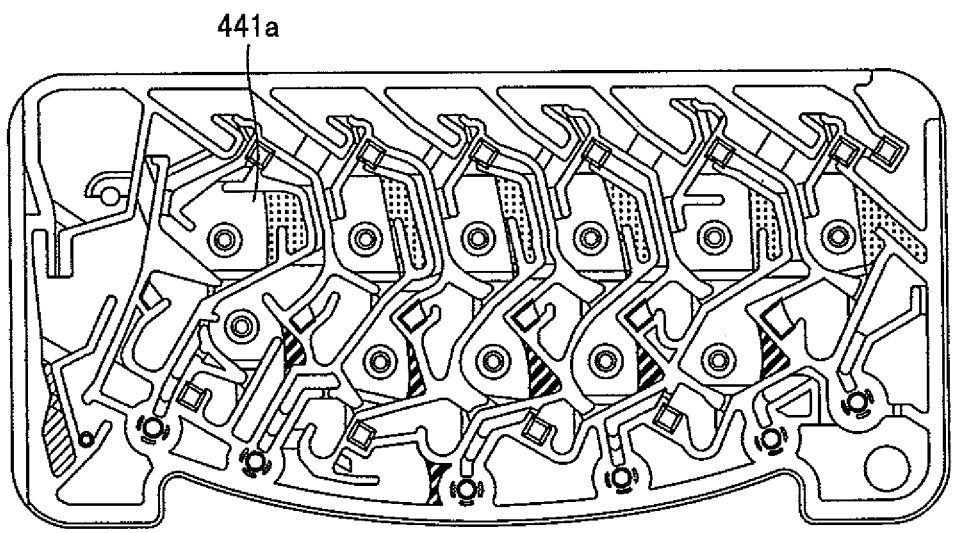
Figure 11:
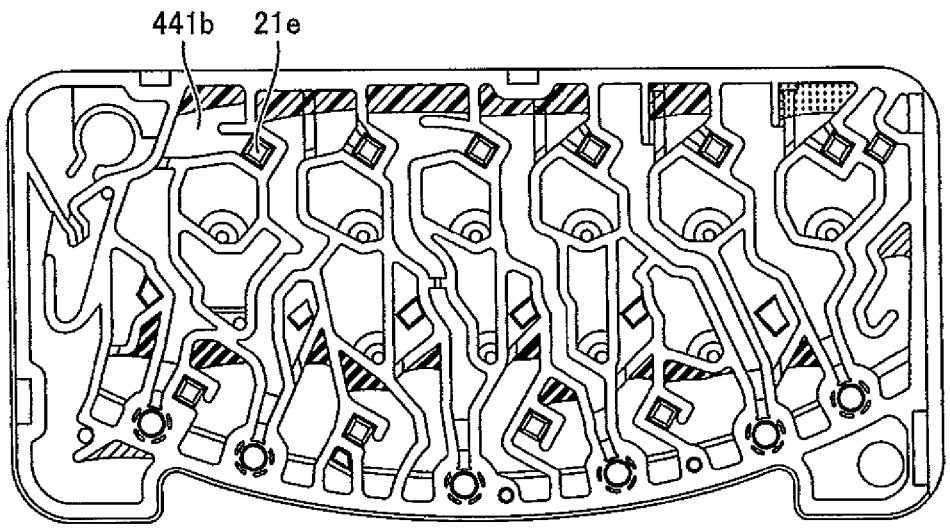
FIG. 11 is a diagram showing a state of a liquid at the top face of the second substrate (the surface on the side of the first substrate) and a state of a liquid at the bottom face thereof (the surface on the side of the third substrate) in a first step of a second mixing process in the fluid treatment using the microchip shown in FIGS. 2 to 4.
Figure 11:
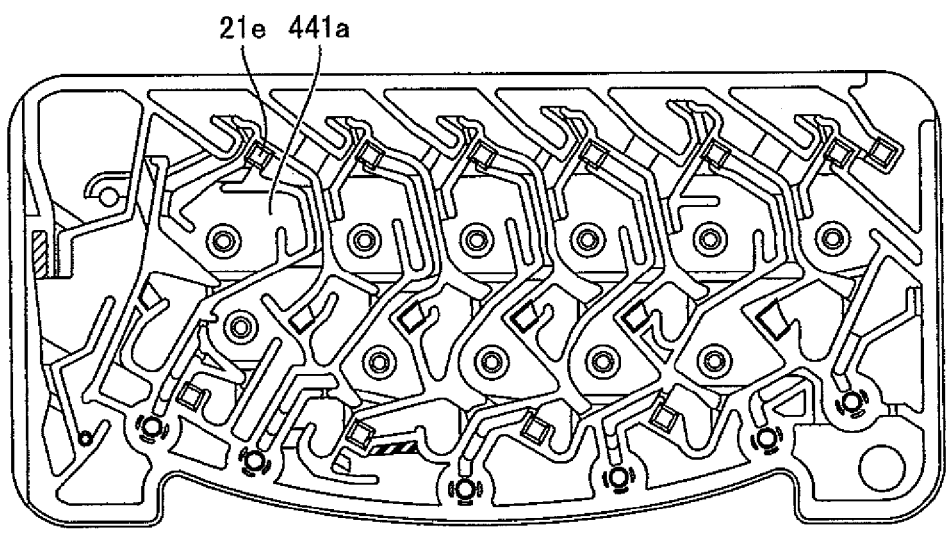

Then, by applying rightward centrifugal force, the liquid mixture is further mixed with the liquid reagent remaining in mixing unit 441a [see a second step in the first mixing process in FIG. 10 (b)]. These first step and second step are performed a plurality of times as necessary in order to reliably achieve mixing. Eventually, a state similar to that shown in FIG. 10 is obtained.

(6) Second Mixing Process

Then, upward centrifugal force is applied. Thus, the liquid mixture in mixing unit 441a reaches mixing unit 441b in the upper fluid circuit via a through hole 21e, whereas the other measured liquid reagent (the liquid reagent held in reagent receptacle unit 301b) also reaches mixing unit 441b via through hole 21e, so that they are mixed together [a first step of a second mixing process. See FIG. 11 (a)]. It is noted that presence of the liquid mixture in the mixing unit may be checked at this stage by irradiating each mixing unit with light and measuring intensity of reflected light.

Figure 12:
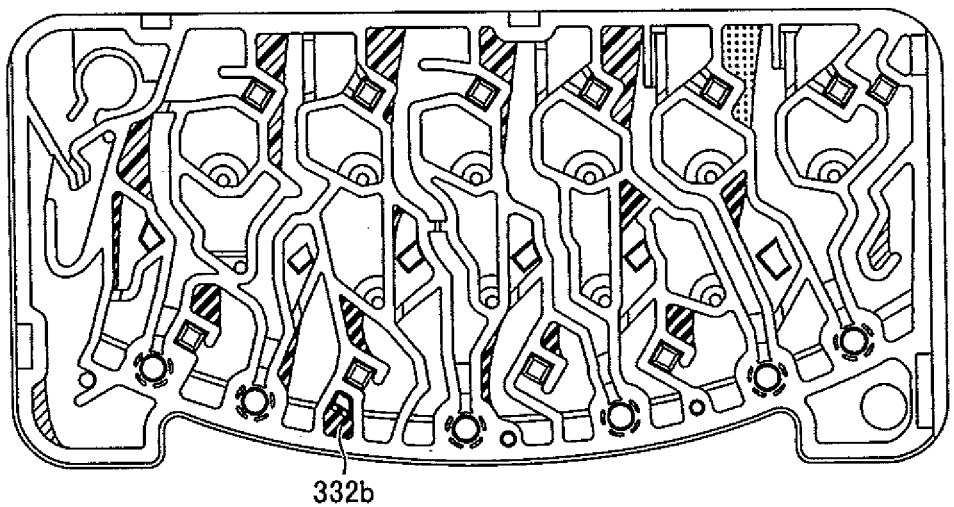
FIG. 12 is a diagram showing a state of a liquid at the top face of the second substrate (the surface on the side of the first substrate) and a state of a liquid at the bottom face thereof (the surface on the side of the third substrate) in a second step of the second mixing process in the fluid treatment using the microchip shown in FIGS. 2 to 4.
Figure 12:
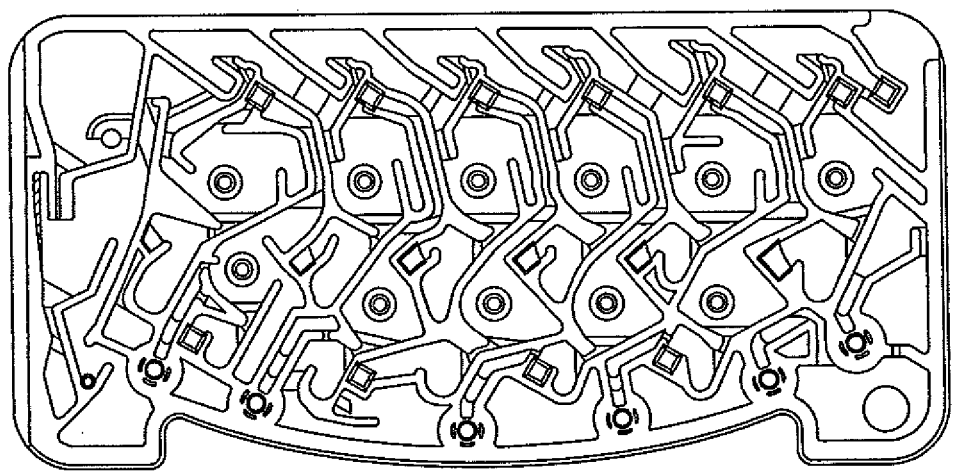
Figure 13:
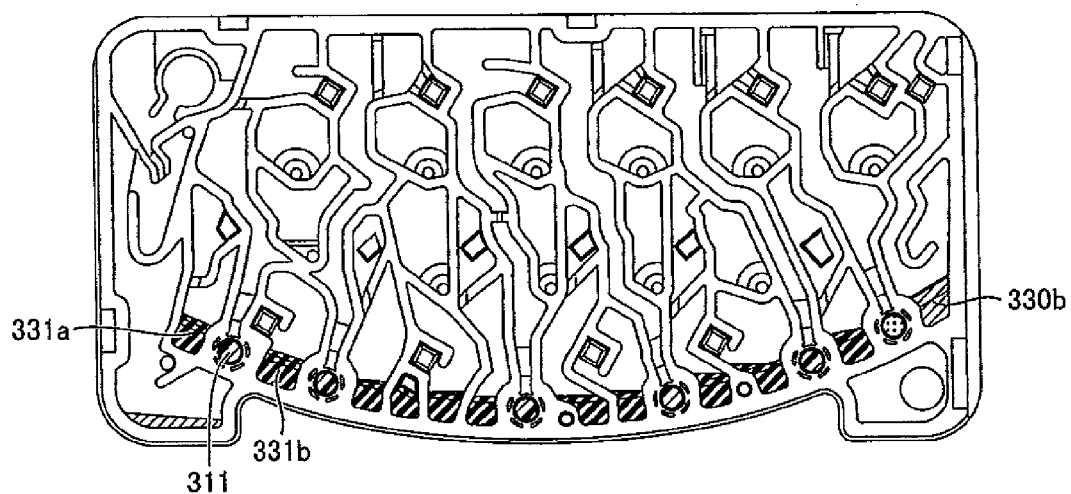
FIG. 13 is a diagram showing a state of a liquid at the top face of the second substrate (the surface on the side of the first substrate) and a state of a liquid at the bottom face thereof (the surface on the side of the third substrate) in a detection unit introduction process in the fluid treatment using the microchip shown in FIGS. 2 to 4.
Figure 13:
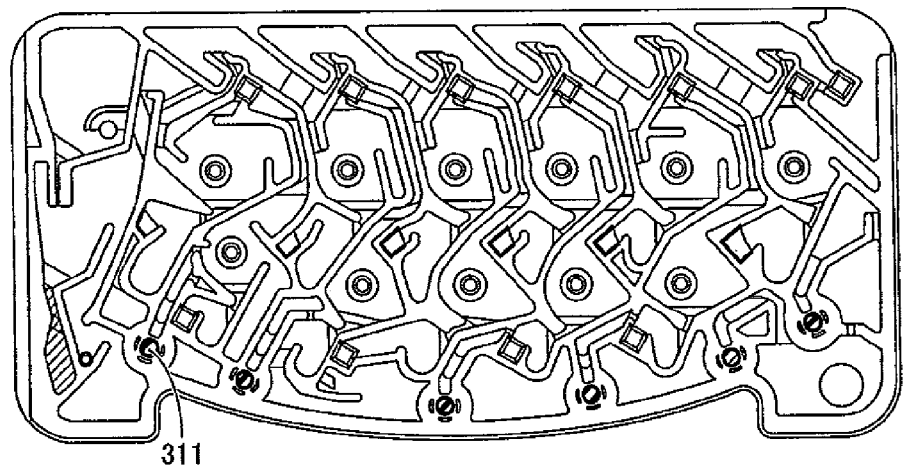

Then, by applying leftward centrifugal force, the liquid mixture moves and mixing is promoted as shown in FIG. 12 (a) [a second step of the second mixing process. See FIG. 12 (a)]. In addition, this leftward centrifugal force also causes the liquid reagent to be stored in overflow reagent storage unit 332b [see FIG. 12 (a)]. These first step and second step are performed a plurality of times as necessary in order to reliably achieve mixing. Eventually, a state similar to that shown in FIG. 12 is obtained.

(7) Detection Unit Introduction Process

Lastly, downward centrifugal force is applied. Thus, the liquid mixture is introduced into detection unit 311 [which is also the case with other liquid mixtures, see FIGS. 13 (a) and 13 (b)]. In addition, overflow reagent storage units 331a, 331b and overflow liquid storage unit 330b have a liquid reagent or a plasma component stored therein, which is also the case with other overflow reagent storage units. The liquid mixture with which the detection unit is filled is subjected to optical measurement for test and analysis. For example, light is emitted in a direction substantially perpendicular to the surface of the microchip and light transmitting therethrough is measured, to thereby detect or the like a specific component in the liquid mixture. Furthermore, here, overflow liquid storage unit 330b and each overflow reagent storage unit are irradiated with light and intensity of reflected light is measured, to thereby check absence or presence of a plasma component or a liquid reagent. Although checking of presence/absence of a plasma component or a liquid reagent does not necessarily have to be carried out at this stage, it is preferable to check presence/absence of a plasma component or a liquid reagent after the detection unit introduction process for simplification of operations, because it is at this stage that the plasma component or the liquid reagent can be stored in all of the overflow liquid storage units and the overflow reagent storage units.

Second Embodiment

Figure 14:
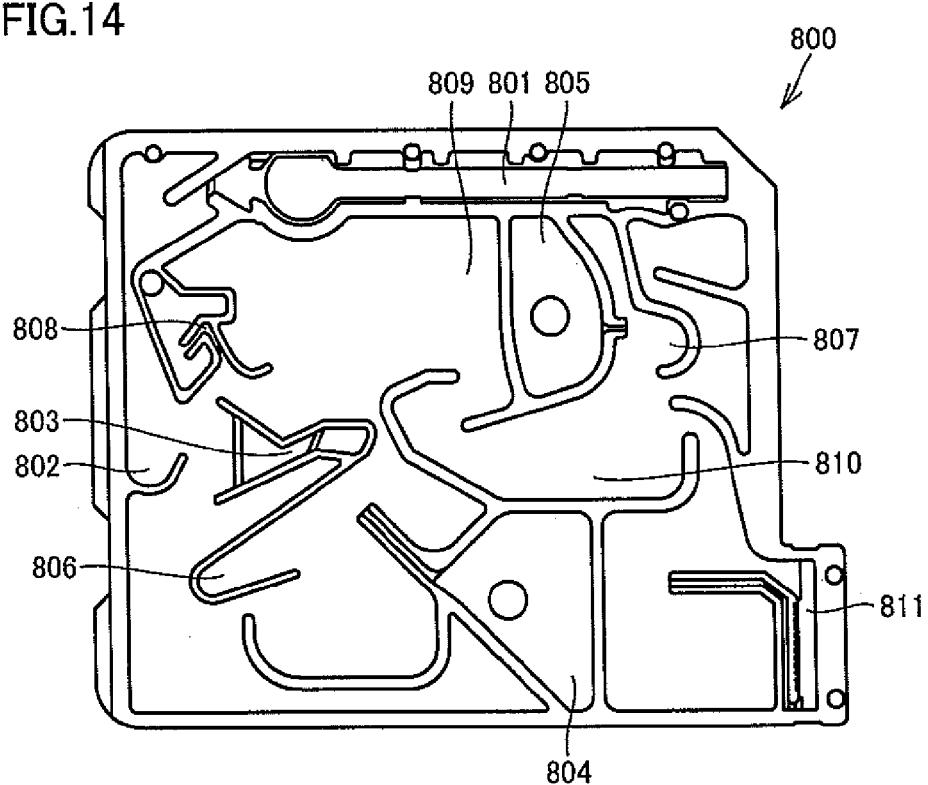
FIG. 14 is a top view showing another example of the microchip according to the present invention.

FIG. 14 is a top view showing another example of the microchip according to the present invention. A microchip 800 shown in FIG. 14 is formed of a stack of a first substrate which is a black substrate and a transparent second substrate including a groove on a substrate surface, and FIG. 14 is a top view when viewed from a side of the second substrate. Microchip 800 has a "single-layered" fluid circuit consisting of a space constituted of a groove on the second substrate and a surface of the first substrate on a side of the second substrate.

Referring to FIG. 14, a fluid circuit in microchip 800 in the present embodiment is mainly constituted of a sample tube storage portion 801 for storing a sample tube (a capillary or the like) storing a specimen (whole blood or the like); a specimen measurement unit 802 for measuring a specimen; a separation unit 803 for separating a second component from the measured specimen and extracting a first component (a component to be mixed with a liquid reagent); reagent receptacle units 804, 805 for holing liquid reagents R1, R2, respectively, to be mixed with the first component (see also FIG. 15); reagent measurement units 806, 807 for measuring liquid reagents R1, R2, respectively; a first component measurement unit 808 for measuring the separated first component; mixing units 809, 810 for mixing the first component and the liquid reagent with each other; and a detection unit 811 for storing a liquid mixture of the first component and liquid reagents R1 and R2 for optical measurement. It is noted that microchip 800 in the present embodiment does not have a flow rate restriction unit.

One example of fluid treatment with the use of microchip 800 in the present embodiment will be described with reference to FIGS. 15 to 27. FIGS. 15 to 27 each show a state (a position or the like) of a liquid within the microchip in each process of the fluid treatment. Though a case where a specimen is whole blood will be described below by way of example, a type of the specimen is not limited thereto.

Figure 15:
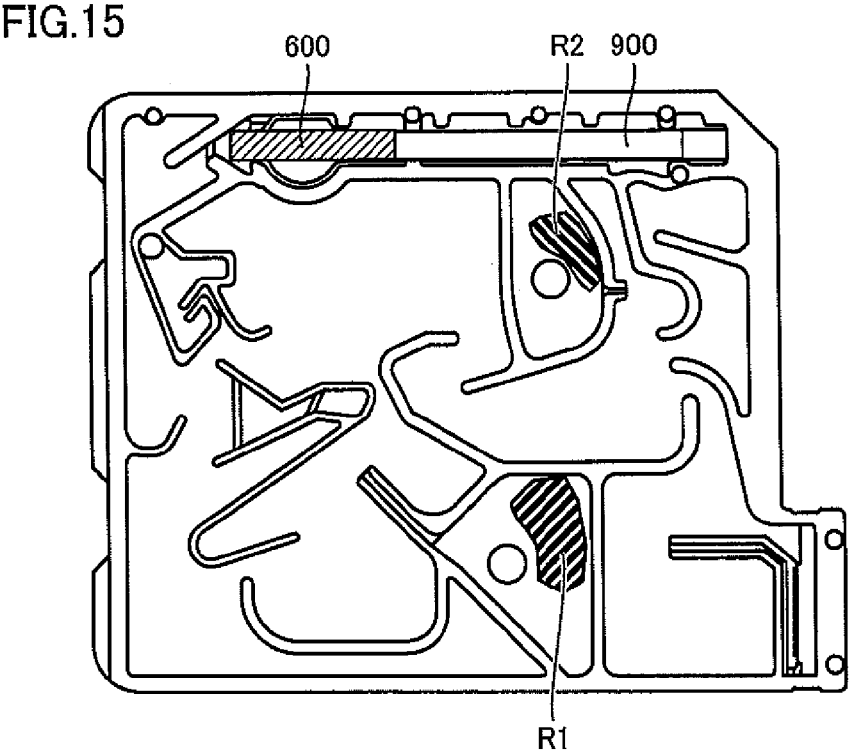
FIG. 15 is a diagram showing a state of a liquid in a sample tube storage process in the fluid treatment using the microchip shown in FIG. 14.
Figure 16:
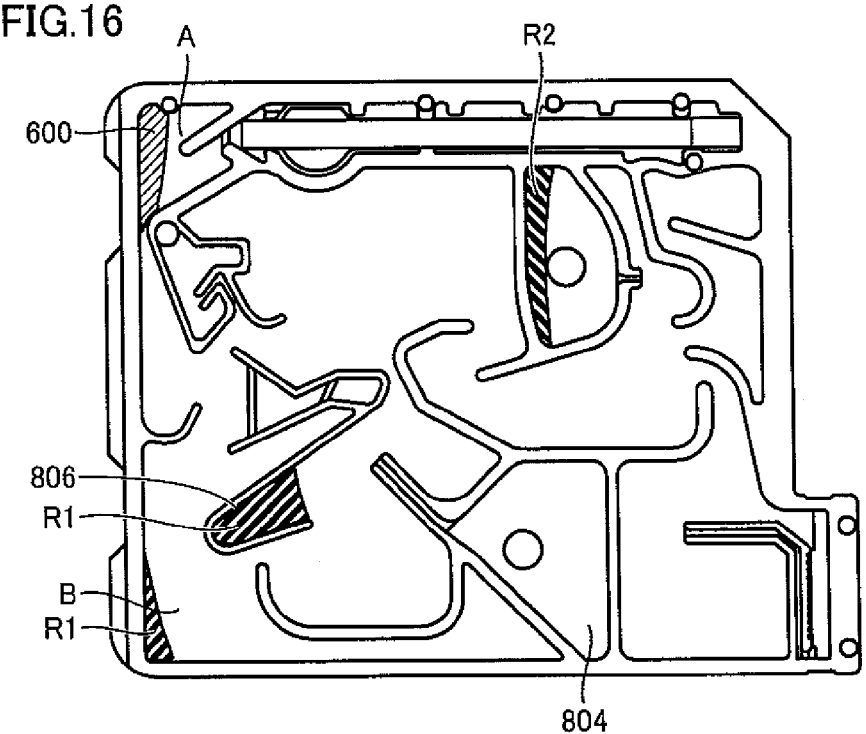
FIG. 16 is a diagram showing a state of a liquid in a reagent measurement process in the fluid treatment using the microchip shown in FIG. 14.

Initially, a sample tube 900 (such as a capillary) containing whole blood 600 is stored in sample tube storage portion 801 (a sample tube storage process, FIG. 15). It is noted that reagent receptacle units 804, 805 of microchip 800 hold in advance liquid reagents R1, R2, respectively. Then, centrifugal force is applied to the microchip in the state shown in FIG. 15 in a leftward direction in FIG. 15 (hereinafter simply referred to as leftward, which is also the case with FIGS. 16 to 27 and is to also similarly be understood with regard to other directions) (a reagent measurement process, FIG. 16). Thus, whole blood within sample tube 900 is exhausted to a region A. In addition, liquid reagent R1 is introduced in reagent measurement unit 806 and measured. Liquid reagent R1 overspilt from reagent measurement unit 806 is stored in a region B.

Figure 17:
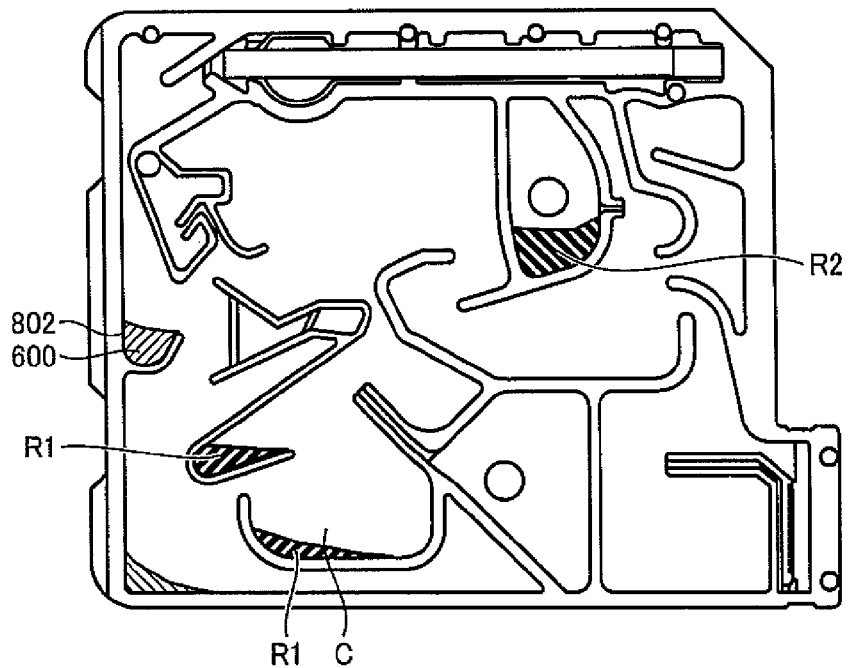
FIG. 17 is a diagram showing a state of a liquid in a whole blood measurement process in the fluid treatment using the microchip shown in FIG. 14.

Then, downward centrifugal force is applied (a whole blood measurement process, FIG. 17). Thus, whole blood 600 is introduced in specimen measurement unit 802 and measured. Whole blood 600 overspilt from specimen measurement unit 802 is stored in region B. In addition, a part of measured liquid reagent R1 moves to a region C.

Figure 18:
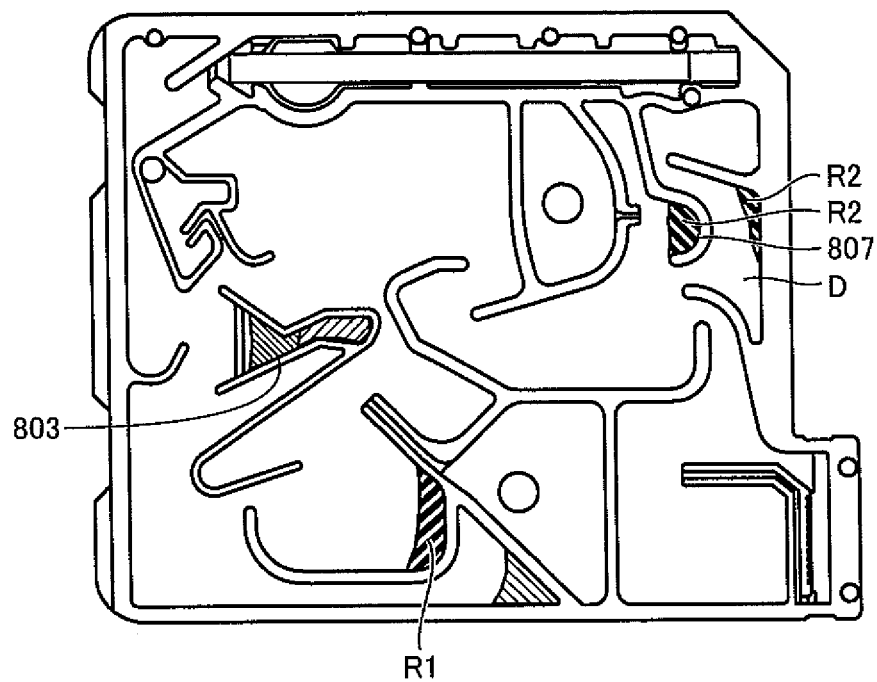
FIG. 18 is a diagram showing a state of a liquid in a plasma separation process in the fluid treatment using the microchip shown in FIG. 14.

Then, rightward centrifugal force is applied (a plasma separation process, FIG. 18). Thus, a total amount of measured whole blood 600 is introduced in separation unit 803. Whole blood 600 introduced in separation unit 803 is centrifuged in separation unit 803 and separated into a plasma component (upper layer) and a hemocyte component (lower layer). In addition, owing to this rightward centrifugal force, liquid reagent R2 is introduced in reagent measurement unit 807 and measured. Liquid reagent R2 overspilt from reagent measurement unit 807 is stored in a region D.

Figure 19:
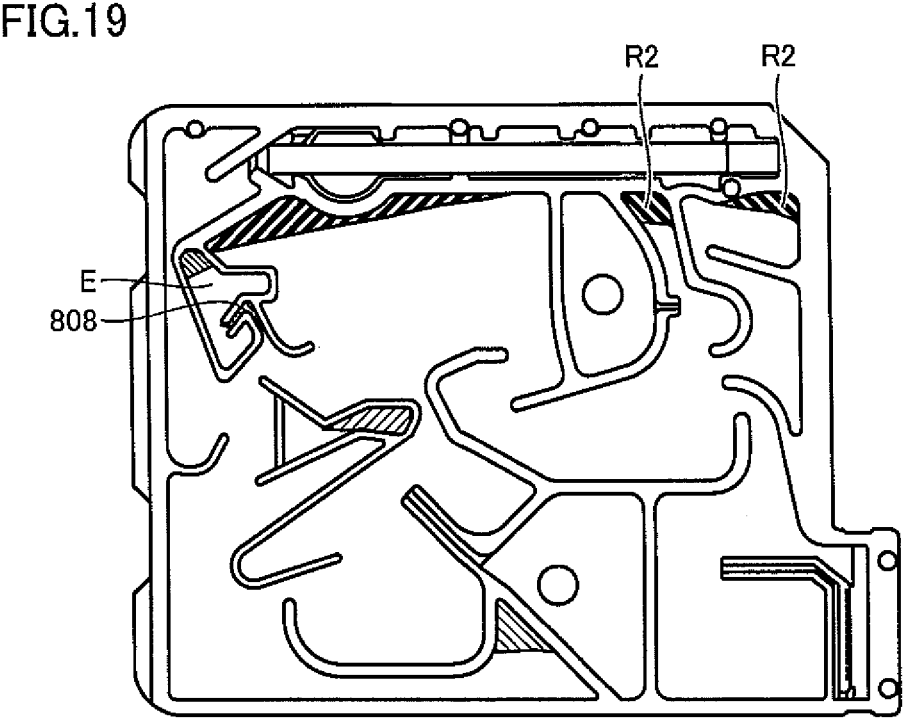
FIG. 19 is a diagram showing a state of a liquid in a plasma component measurement process in the fluid treatment using the microchip shown in FIG. 14.

Then, upward centrifugal force is applied (a plasma component measurement process, FIG. 19). Thus, the plasma component separated in separation unit 803 is introduced in first component measurement unit 808 and measured. The plasma component overspilt from first component measurement unit 808 is stored in a region E.

Figure 20:
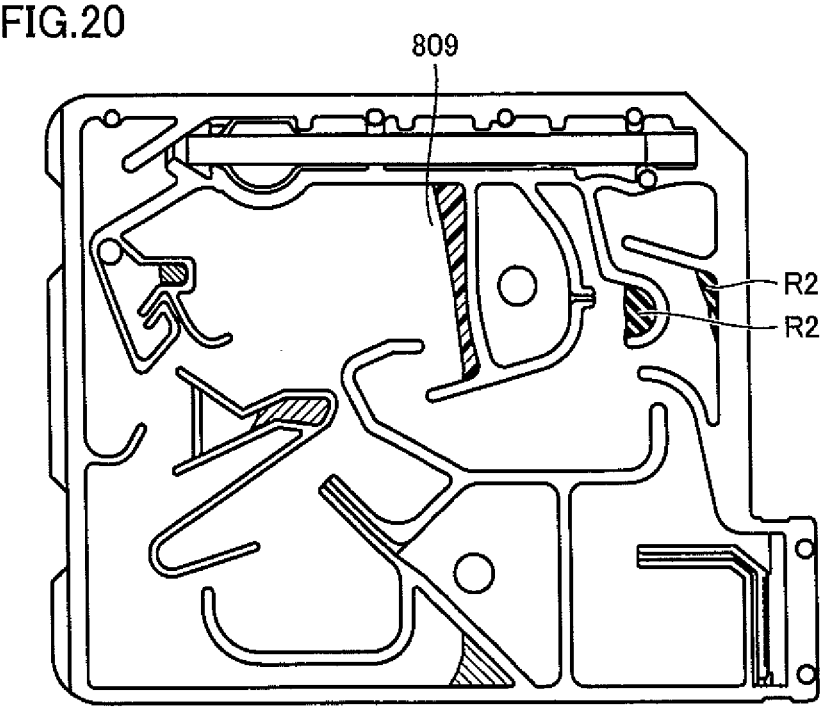
FIG. 20 is a diagram showing a state of a liquid in a first step of a first mixing process in the fluid treatment using the microchip shown in FIG. 14.
Figure 21:
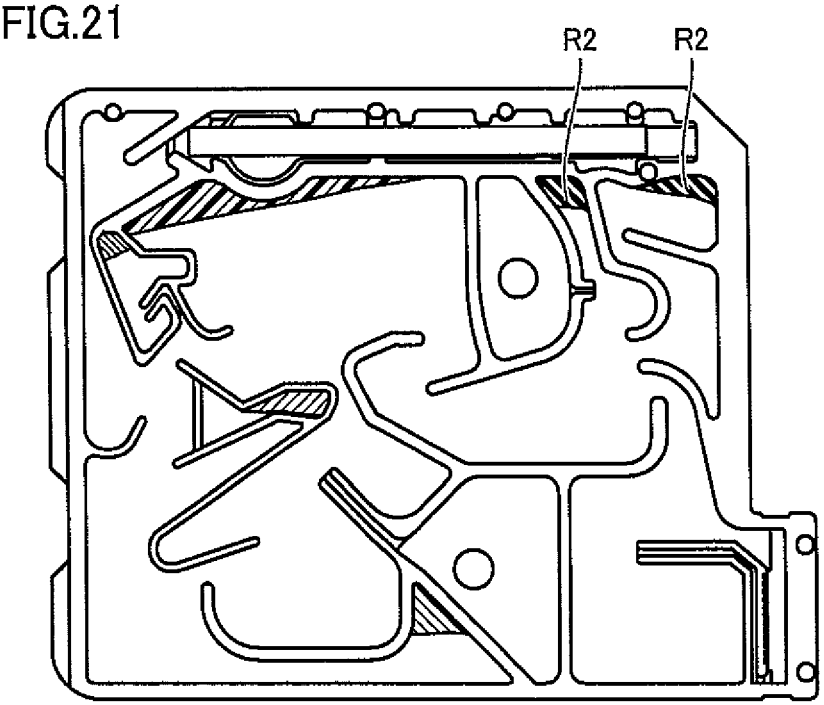
FIG. 21 is a diagram showing a state of a liquid in a second step of the first mixing process in the fluid treatment using the microchip shown in FIG. 14.
Figure 22:
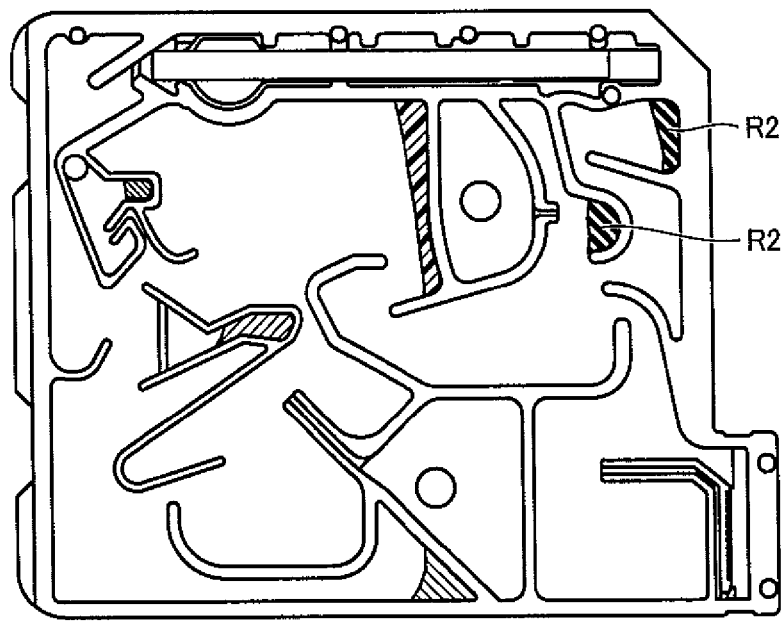
FIG. 22 is a diagram showing a state of a liquid in a third step of the first mixing process in the fluid treatment using the microchip shown in FIG. 14.

Then, rightward centrifugal force is applied (a first step of a first mixing process, FIG. 20). Thus, measured liquid reagent R1 and the plasma component measured in first component measurement unit 808 are mixed with each other in mixing unit 809. Then, upward centrifugal force is applied (a second step of the first mixing process, FIG. 21) and rightward centrifugal force is further applied (a third step of the first mixing process, FIG. 22), so as to promote mixing between liquid reagent R1 and the plasma component.

Figure 23:
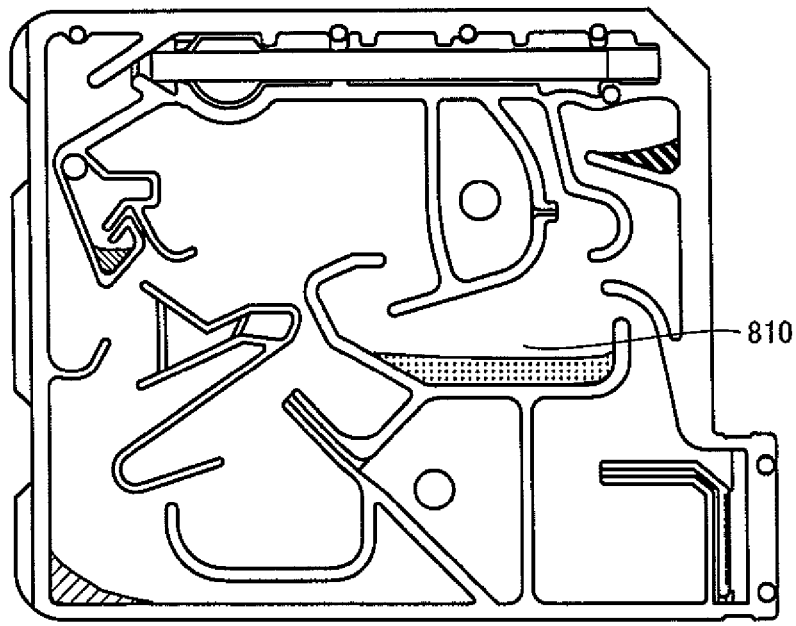
FIG. 23 is a diagram showing a state of a liquid in a first step of a second mixing process in the fluid treatment using the microchip shown in FIG. 14.
Figure 24:
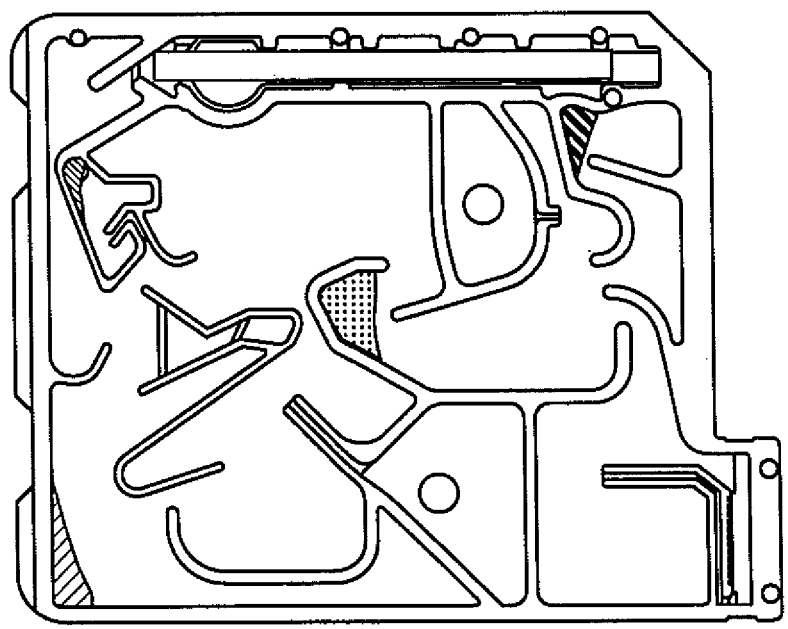
FIG. 24 is a diagram showing a state of a liquid in a second step of the second mixing process in the fluid treatment using the microchip shown in FIG. 14.
Figure 25:
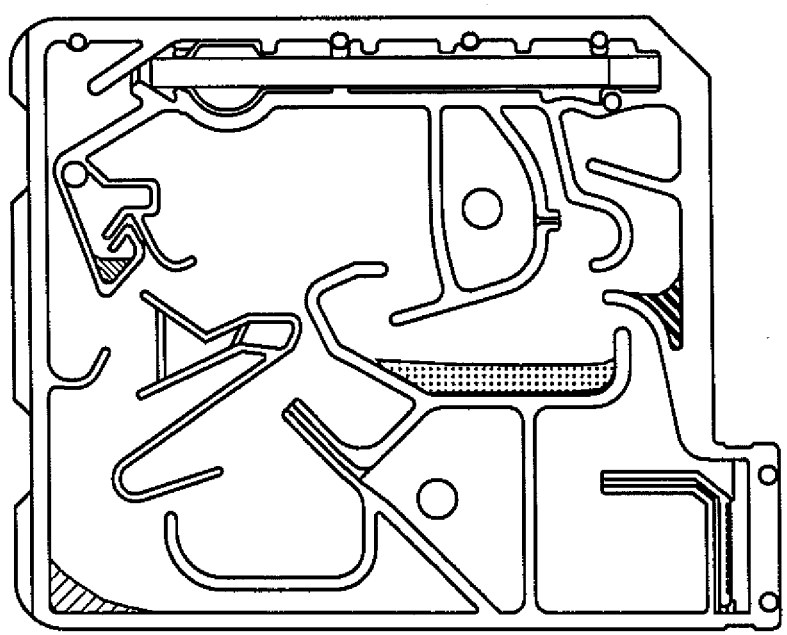
FIG. 25 is a diagram showing a state of a liquid in a third step of the second mixing process in the fluid treatment using the microchip shown in FIG. 14.
Figure 26:
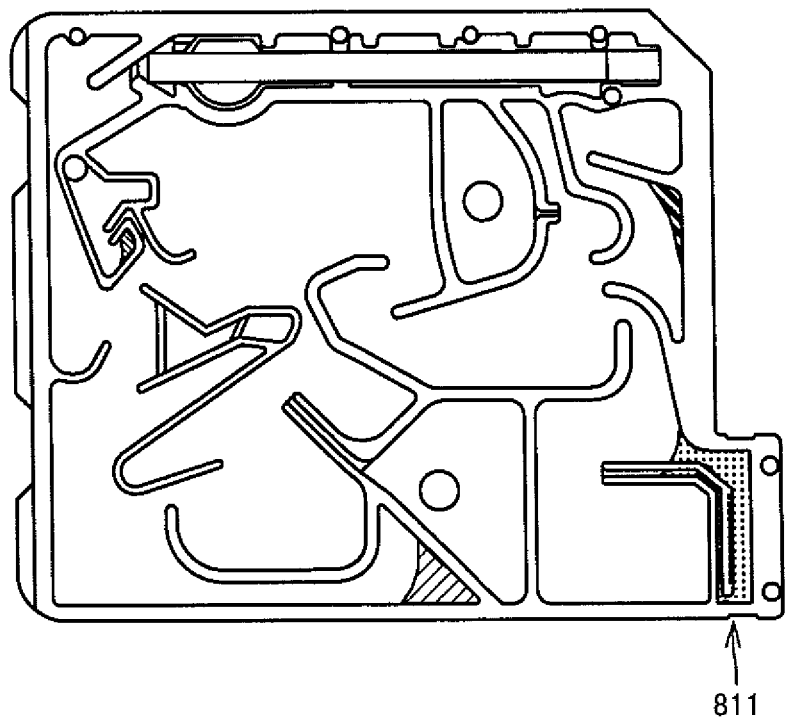
FIG. 26 is a diagram showing a state of a liquid in a detection unit introduction process in the fluid treatment using the microchip shown in FIG. 14.

Then, downward centrifugal force is applied (a first step of a second mixing process, FIG. 23). Thus, the liquid mixture of liquid reagent R1 and the plasma component, and measured liquid reagent R2 are mixed in mixing unit 810. Then, leftward centrifugal force is applied (a second step of the second mixing process, FIG. 24) and downward centrifugal force is further applied (a third step of the second mixing process, FIG. 25), so as to promote mixing with liquid reagent R2.

Figure 27:
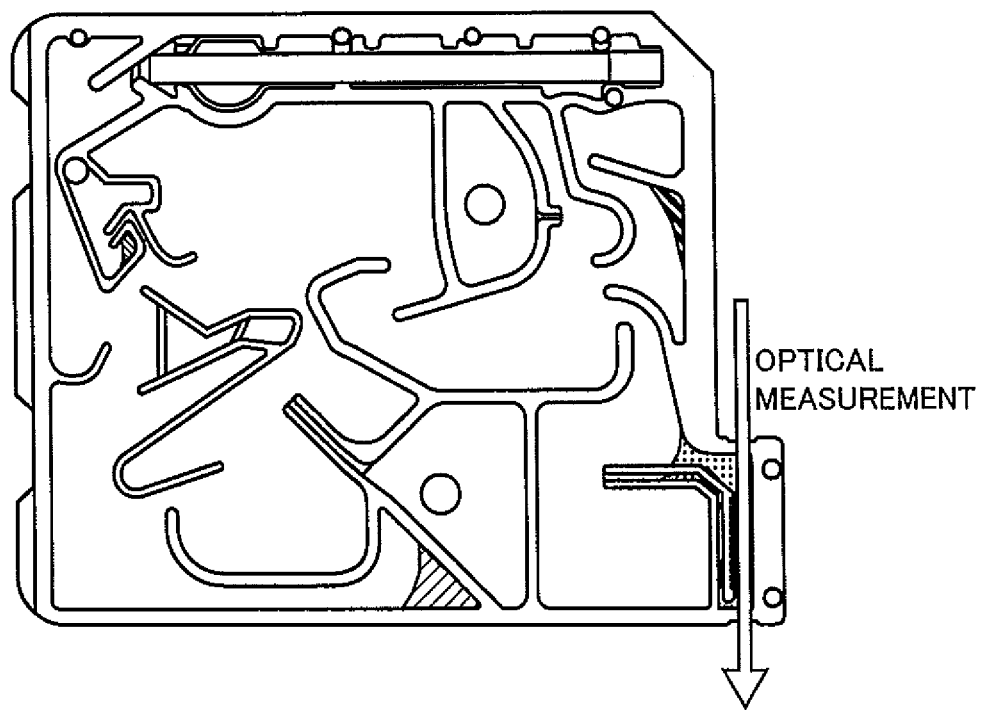
FIG. 27 is a diagram showing a manner in which the detection unit of the microchip shown in FIG. 26 is irradiated with light for optical measurement.
Figure 28:
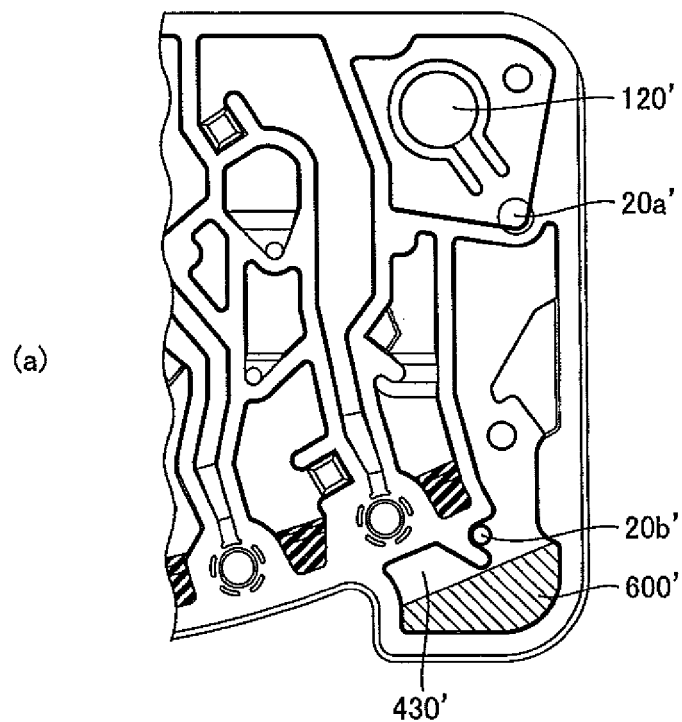
FIG. 28 is a top view and a bottom view showing in an enlarged manner, a part of a microchip including fluid circuits in two layers disclosed in PTD 1.
Figure 28:
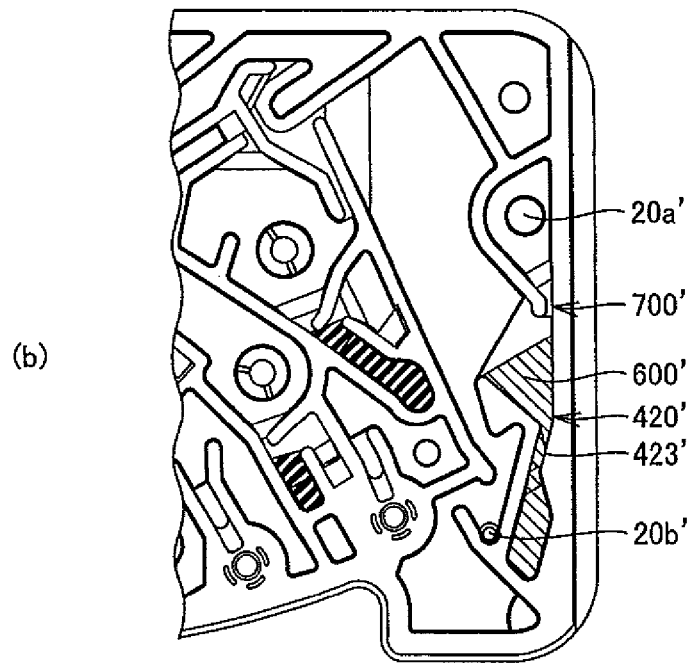

Finally, rightward centrifugal force is applied, so that the liquid mixture of the plasma component, liquid reagent R1, and liquid reagent R2 is introduced in detection unit 811 (a detection unit introduction process, FIG. 26) and detection unit 811 is irradiated with light for optical measurement (FIG. 27).

Though the microchip according to the present invention has been described above with reference to preferred embodiments, the microchip according to the present invention is not limited to the embodiments above. For example, the microchip according to the present invention does not necessarily have to be a multi-test chip but it may be a single-test chip conducting one type of test or analysis alone. In addition, the present invention does not have to have all of the sites described above and any one or more sites may be absent therein. Alternatively, other sites not mentioned above may be provided. Furthermore, the number of sites in the microchip is not particularly limited either.

In addition, the fluid circuit in the microchip according to the present invention is not limited to the structure in the embodiments above but it can adopt various structures.

REFERENCE SIGNS LIST 11a, 11b, 16a, 16b channel; 20a', 20b', 21a, 21b, 21e, 21d, 21e, 26a, 30 through hole; 100, 800 microchip; 101 first substrate; 102 second substrate; 103 third substrate; 110 reagent inlet; 120, 120' specimen inlet; 301a, 301b, 302a, 302b, 303a, 303b, 304a, 304b, 305a, 305b, 306a, 804, 805 reagent receptacle unit; 311, 312, 313, 314, 315, 316, 811 detection unit; 330a, 330b overflow liquid storage unit; 331a, 331b, 332a, 332b, 333a, 333b, 334a, 334b, 335a, 335b, 336a overflow reagent storage unit; 401, 402, 403, 404, 405, 406, 808 first component measurement unit; 411a, 411b, 412a, 412b, 413a, 413b, 414a, 414b, 415a, 415b, 416a, 806, 807 reagent measurement unit; 420, 803 separation unit; 420' hemocyte separation unit; 421 opening of separation unit; 422 first component storage unit; 423, 423' narrow portion; 424 second component storage unit; 430' waste reservoir; 441a, 441b, 809, 810 mixing unit; 500, 802 specimen measurement unit; 600, 600' whole blood; 700, 700' flow rate restriction unit; 701 stand-by portion; 801 sample tube storage portion; and 900 sample tube.

The invention claimed is:

1. A microchip comprising:
a first substrate;
a second substrate stacked on said first substrate and having a first groove on a first surface of the second substrate and a second groove on a second opposite surface of the second substrate;
a third substrate stacked on said second substrate;
a first fluid circuit including a space defined by said first groove and a surface of said first substrate on a first side of said second substrate;
a second fluid circuit including a space defined by said second groove and a surface of said third substrate on a second side of said second substrate; and
a specimen inlet for introducing in one of said fluid circuits, a specimen containing a first component and a second component different in specific gravity from each other, said first and second fluid circuits collectively comprising:
a specimen measurement unit connected to said specimen inlet and having a prescribed volume for measuring the specimen introduced through said specimen inlet, and
a separation unit which is a site connected to said specimen measurement unit and having a capacity capable of storing a total amount of the measured specimen, for storing the total amount of the measured specimen and separating said first component and said second component in the stored specimen from each other, and
said separation unit having a structure including (i) an opening for accepting the measured specimen, (ii) a first component storage unit for storing the separated first component, and (iii) a second component storage unit for storing the separated second component, arranged in this order,
said first component storage unit and said second component storage unit being connected to each other through a narrow portion having a narrower width than those of said first component storage unit and said second component storage unit, and
a volume of said first component storage unit being greater than a volume of the measured specimen.

2. The microchip according to claim 1, wherein said first fluid circuit has said specimen measurement unit and said second fluid circuit has said separation unit.

* * * * *